US007198921B2

(12) United States Patent
Miura et al.

(10) Patent No.: US 7,198,921 B2
(45) Date of Patent: Apr. 3, 2007

(54) PROCESS FOR PRODUCING PROTEIN WITH REDUCTION OF ACIDIC SUGAR CHAIN AND GLYCOPROTEIN PRODUCED THEREBY

(75) Inventors: Masami Miura, Tokyo (JP); Masaaki Hirose, Tokyo (JP); Taeko Miwa, Tokyo (JP); Hiroyuki Irie, Tokyo (JP); Shinobu Kuwae, Tokyo (JP); Kenmi Miyano, Tokyo (JP); Wataru Otani, Tokyo (JP); Hideyuki Ohi, Tokyo (JP)

(73) Assignee: Mitsubishi Pharma Corporation, Osaka (JP)

( * ) Notice: Subject to any disclaimer, the term of this patent is extended or adjusted under 35 U.S.C. 154(b) by 604 days.

(21) Appl. No.: 10/276,075

(22) PCT Filed: May 16, 2001

(86) PCT No.: PCT/JP01/04070

§ 371 (c)(1),
(2), (4) Date: Dec. 9, 2002

(87) PCT Pub. No.: WO01/88143

PCT Pub. Date: Nov. 22, 2001

(65) Prior Publication Data

US 2004/0014170 A1 Jan. 22, 2004

(51) Int. Cl.
| C12P 19/04 | (2006.01) |
| C12P 21/02 | (2006.01) |
| C12N 1/18 | (2006.01) |
| C07H 21/04 | (2006.01) |
| C12N 14/39 | (2006.01) |

(52) U.S. Cl. .................... 435/72; 435/69.1; 435/320.1; 435/254.23; 435/193; 536/23.7

(58) Field of Classification Search .............. 435/69.1; 530/395
See application file for complete search history.

(56) References Cited

U.S. PATENT DOCUMENTS

2002/0137134 A1* 9/2002 Gerngross .................. 435/69.1

FOREIGN PATENT DOCUMENTS

| EP | 0 256 421 | 2/1988 |
| JP | 09-03097 | 1/1997 |
| JP | 9-266792 | 10/1997 |

OTHER PUBLICATIONS

Montesino, R. et al., Characterization of the Oligosaccharides Assembled on the Pichiapastoris-expressed Recombinant Aspartic Protease, Glycobiology, vol. 9, No. 10, pp. 1037-1-43 (1999).
Odani, T. et al, Cloning and Analysis of the MNN4 Gene Required for Phosphorylation of N-linked Oligosaccharides on Saccharomyces Cerevisiae, Glycobiology, vol. 6, No. 8, pp. 805-810 (1996).
Montesino et al., "Variation in N-Linked Oligosaccharide Structures on Heterologous Proteins Secreted by the Methylotrophic Yeast Pichia Pastoris," Protein Expression and Purification, vol. 14, No. 2, Nov. 1998, pp. 197-207.
Carolos et al., "Antibodies from HIV-Positive and AIDS Patients Bind to an HIV Envelope Multivalent Vaccine," Journal of Acquired Immune Deficiency Syndromes, vol. 22, No. 4, Dec. 1999, pp. 317-324.
Martinet et al., "Modification of the Protein Glycosylation Pathway in the Methylotrophic Yeast Pichia Pastoris," Biotechnology Letters, vol. 20, No. 12, Dec. 1998, pp. 1171-1177.
Miele et al., "Characterization of the Acidic Oligosaccharides Assembled on the Pichia Pastoris-Expressed Recombinant Kringle 2 Domain of Human Tissue-Type Plasminogen Activator," Biotechnology and Applied Biochemistry, vol. 26, Oct. 1997, pp. 79-83.
Grinna et al., "Size Distribution and General Structural Features of N-linked Oligosaccharides from the Methylotrophic Yeast, Pichia Pastoris," Yeast, vol. 5, No. 2, Mar. 1989, pp. 107-115.
Miura et al., "Cloning and Characterization in Pichia Patoris of PN01 Gene Required for Phosphomannosylation of N-linked Oligosaccharides," Gene: An International Journal on Genes and Genomes, vol. 324, Jan. 2004, pp. 129-137.
Supplementary European Search Report for European Application No. EP 01 93 0179 dated Sep. 3, 2004.

* cited by examiner

Primary Examiner—Rebecca E. Prouty
Assistant Examiner—Mohammad Meah
(74) Attorney, Agent, or Firm—Kilyk & Bowersox, P.L.L.C.

(57) ABSTRACT

The present invention intends to find out a gene participating in addition of mannose phosphate to a sugar chain of a glycoprotein originating in a yeast belonging to the genus *Pichia* and provide a means of controlling the same. The present invention also intends to provide a process for producing a protein with reduction of an acidic sugar chain by using the thus controlled yeast strain belonging to the genus *Pichia*. Namely, the present invention includes a protein participating in the addition of mannose phosphate to a sugar chain of a glycoprotein; a gene encoding this protein; a mutant of this gene; a vector carrying the mutant gene; a yeast strain belonging to the genus *Pichia* having been transformed by this vector; a process for producing a protein with reduction of an acidic sugar chain by using the transformed yeast strain; and a glycoprotein thus produced.

2 Claims, 10 Drawing Sheets

Strain RH101 (○ ;OD$_{540}$  ● ;amount of rATⅢ produced)
Strain 9G4   (△ ;OD$_{540}$  ▲ ;amount of rATⅢ produced)

Neutral Oligosaccharide---1/10 analyzed

Acidic Oligosaccharide---1/2 analyzed

Fig.10

- ●— Binding reaction of an anti-serum against recombinant human ATⅢ derived from a wild-type yeast with recombinant human ATⅢ d riv d from a wild-type yeast
- ○··· Binding reaction of an anti-serum against recombinant human ATⅢ derived from a PNO1 disruptant with recombinant human ATⅢ derived from a PNO1 disruptant
- ■— Binding reaction of an anti-serum against human ATⅢ derived from plasma with recombinant human ATⅢ derived from a wild-type yeast
- □··· Binding reaction of an anti-serum against human ATⅢ derived from plasma with recombinant human ATⅢ derived from a PNO1 disruptant

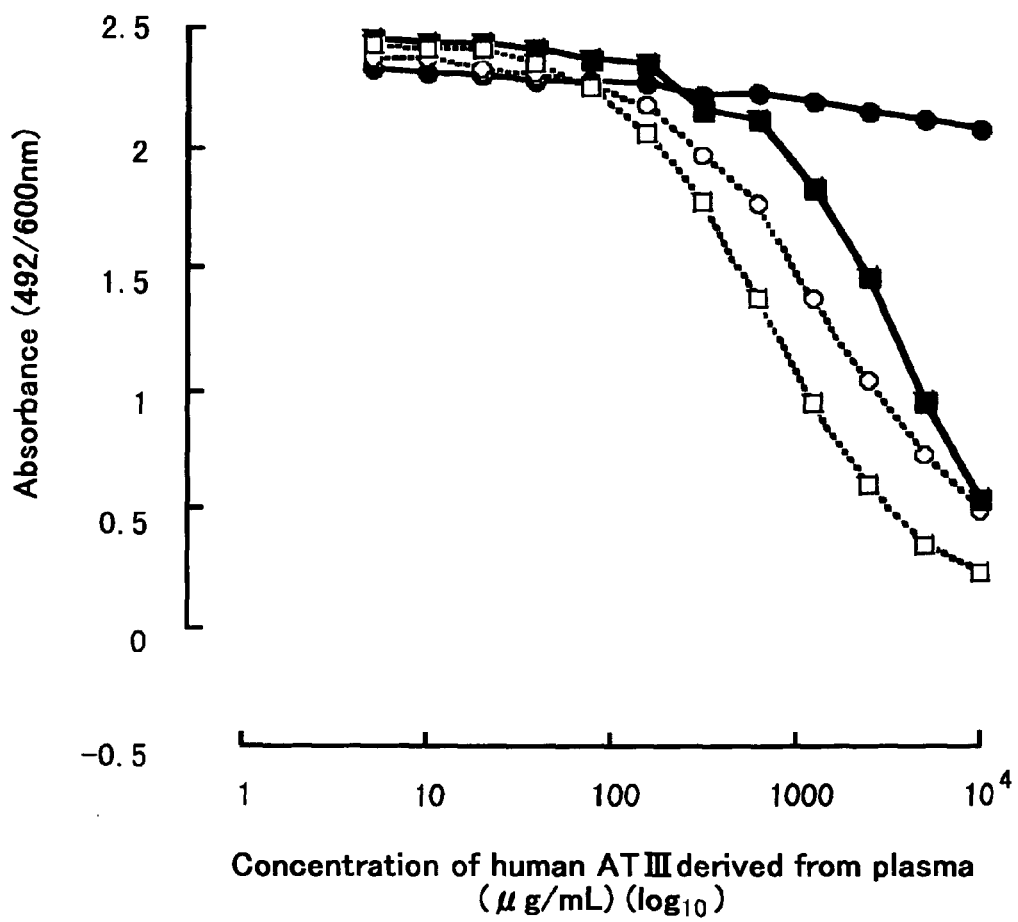

Concentration of human ATⅢ derived from plasma
($\mu$ g/mL) ($\log_{10}$)

SEQUENCE LISTING

<160> NUMBER OF SEQ ID NOS: 5

<210> SEQ ID NO 1
<211> LENGTH: 20
<212> TYPE: PRT
<213> ORGANISM: Pichia pastoris

<400> SEQUENCE: 1

```
Met Thr Leu Arg Ser Ala Ile Lys Ala Arg Thr Ser Lys Gly Leu Ile
 1               5                  10                  15

Gly Ala Val Ile
            20

<210> SEQ ID NO 2
<211> LENGTH: 2632
<212> TYPE: DNA
<213> ORGANISM: Pichia pastoris
<220> FEATURE:
<221> NAME/KEY: CDS
<222> LOCATION: (150)..(2483)

<400> SEQUENCE: 2
gcagtttaat catagcccac tgctaagcca gaattctaat atgtaactac gtacctttcc         60
ttttaataaa tgatctgtat tttccaccta agtagcagat caaattgttc aactttaagt        120
ctttggtccc tcaagcgaga gaacttgcg atg aca ctc agg agt gcc ata aaa          173
                                Met Thr Leu Arg Ser Ala Ile Lys
                                 1               5 gcc aga acc tca aaa gga ctg atc gga gct gtt att ata gcc tca ata          221
Ala Arg Thr Ser Lys Gly Leu Ile Gly Ala Val Ile Ile Ala Ser Ile
     10                  15                  20 ata ttt ttc acc aca gta acc ttc tac gat gaa agc aaa att gtc ggc          269
Ile Phe Phe Thr Thr Val Thr Phe Tyr Asp Glu Ser Lys Ile Val Gly
 25                  30                  35                  40 ata ata aga gtt tct gat act tat aca ggc cat agc gct gta tct tca          317
Ile Ile Arg Val Ser Asp Thr Tyr Thr Gly His Ser Ala Val Ser Ser
                 45                  50                  55 act ttc aat gct tct tcc gtt gtt agt gac aac aag atc aac gga tat          365
Thr Phe Asn Ala Ser Ser Val Val Ser Asp Asn Lys Ile Asn Gly Tyr
             60                  65                  70 gga ctt cct ttg att gac acg gaa tca aat agc cgt tat gag gat cca          413
Gly Leu Pro Leu Ile Asp Thr Glu Ser Asn Ser Arg Tyr Glu Asp Pro
         75                  80                  85 gac gat att tcc att gaa aac gaa ttg cgc tat aga att gcc caa tct          461
Asp Asp Ile Ser Ile Glu Asn Glu Leu Arg Tyr Arg Ile Ala Gln Ser
     90                  95                 100 acc aaa gag gaa gaa aac atg tgg aaa ctc gat acc act ctc acg gaa          509
Thr Lys Glu Glu Glu Asn Met Trp Lys Leu Asp Thr Thr Leu Thr Glu
105                 110                 115                 120 gca agc ttg aaa atc ccc aac ata cag tcg ttt gag ctg cag ccg ttc          557
Ala Ser Leu Lys Ile Pro Asn Ile Gln Ser Phe Glu Leu Gln Pro Phe
                125                 130                 135 aaa gaa aga ctt gat aat tca ctt tac aat tct aag aac ata gga aac          605
Lys Glu Arg Leu Asp Asn Ser Leu Tyr Asn Ser Lys Asn Ile Gly Asn
            140                 145                 150 ttt tac ttc tat gac cca agg ctt aca ttc tca gtt tac ttg aag tat          653
Phe Tyr Phe Tyr Asp Pro Arg Leu Thr Phe Ser Val Tyr Leu Lys Tyr
        155                 160                 165 atc aag gat aaa ttg gcc tct gga agc aca aca aat ctt aca ata ccc          701
Ile Lys Asp Lys Leu Ala Ser Gly Ser Thr Thr Asn Leu Thr Ile Pro
    170                 175                 180 ttc aac tgg gca cat ttt aga gat tta tcg tca ctg aat cct tat ttg          749
Phe Asn Trp Ala His Phe Arg Asp Leu Ser Ser Leu Asn Pro Tyr Leu
185                 190                 195                 200 gac ata aaa caa gaa gat aag gtc gca tgt gat tac ttt tat gaa tca          797
Asp Ile Lys Gln Glu Asp Lys Val Ala Cys Asp Tyr Phe Tyr Glu Ser
                205                 210                 215 agt aat aaa gac aaa cga aaa ccc acg ggt aac tgt att gag ttt aaa          845
Ser Asn Lys Asp Lys Arg Lys Pro Thr Gly Asn Cys Ile Glu Phe Lys
```

-continued

|  |  |  |
|---|---|---|
| 220 | 225 | 230 |

| | |
|---|---|
| gat gtt cgt gat gag cac ctg ata cag tat ggg att tca tca aaa gac<br>Asp Val Arg Asp Glu His Leu Ile Gln Tyr Gly Ile Ser Ser Lys Asp<br>235                             240                      245 | 893 |
| cat cta cct ggt cct ttt att tta aag tca ctt gga att ccc atg cag<br>His Leu Pro Gly Pro Phe Ile Leu Lys Ser Leu Gly Ile Pro Met Gln<br>250                             255                      260 | 941 |
| cat aca gcc aag cga ctg gaa tca aat ctt tat cta tta acc ggt gcg<br>His Thr Ala Lys Arg Leu Glu Ser Asn Leu Tyr Leu Leu Thr Gly Ala<br>265                             270                             280 | 989 |
| cca gtt cca ctt tca tta agt ttc atg act aaa aag gga tta tac caa<br>Pro Val Pro Leu Ser Leu Ser Phe Met Thr Lys Lys Gly Leu Tyr Gln<br>                        285                      290                      295 | 1037 |
| gtt gga gtt gac caa aca gga aaa ctt gat cca aac att gct cgt act<br>Val Gly Val Asp Gln Thr Gly Lys Leu Asp Pro Asn Ile Ala Arg Thr<br>                  300                      305                      310 | 1085 |
| gaa cta tgg gag ttt tac aaa aat ggg aaa gaa aac ctt caa ttt aat<br>Glu Leu Trp Glu Phe Tyr Lys Asn Gly Lys Glu Asn Leu Gln Phe Asn<br>                  315                      320                      325 | 1133 |
| gca caa gag gag cta tct cac ctg ata gag aca gtc cct tca tct agt<br>Ala Gln Glu Glu Leu Ser His Leu Ile Glu Thr Val Pro Ser Ser Ser<br>330                             335                      340 | 1181 |
| aac tca tcc agt gga gaa ggc tat ttc act act gaa tta aag gag aac<br>Asn Ser Ser Ser Gly Glu Gly Tyr Phe Thr Thr Glu Leu Lys Glu Asn<br>345                             350                      355                      360 | 1229 |
| aac ttt gag ttg ccc ctg agt aag aat gat ttt acc ttt gat gat tcc<br>Asn Phe Glu Leu Pro Leu Ser Lys Asn Asp Phe Thr Phe Asp Asp Ser<br>                  365                      370                      375 | 1277 |
| gag gtc gag tca ttg att aaa ggt tta tct gaa cag gac ttg gac ctt<br>Glu Val Glu Ser Leu Ile Lys Gly Leu Ser Glu Gln Asp Leu Asp Leu<br>                  380                      385                      390 | 1325 |
| cat acc cag aga tac aaa gaa tct ttg cag tac tct ttt gcg act cga<br>His Thr Gln Arg Tyr Lys Glu Ser Leu Gln Tyr Ser Phe Ala Thr Arg<br>                  395                      400                      405 | 1373 |
| gag aat gac gtg aag aaa tac ttt tat gag gcc aga atg att atc aat<br>Glu Asn Asp Val Lys Lys Tyr Phe Tyr Glu Ala Arg Met Ile Ile Asn<br>410                             415                      420 | 1421 |
| act gtt aac aaa gaa ggt gga gcg cat tat gac tgg agg ttt ttc aat<br>Thr Val Asn Lys Glu Gly Gly Ala His Tyr Asp Trp Arg Phe Phe Asn<br>425                             430                      435                      440 | 1469 |
| gga gcc atg aat cat gaa agt tcc ggt ttt act gag gaa gaa aga caa<br>Gly Ala Met Asn His Glu Ser Ser Gly Phe Thr Glu Glu Glu Arg Gln<br>                  445                      450                      455 | 1517 |
| ctg aga aag aga tct gtt ttg cat cgt tta ttg cga aac tgg ctt gta<br>Leu Arg Lys Arg Ser Val Leu His Arg Leu Leu Arg Asn Trp Leu Val<br>                  460                      465                      470 | 1565 |
| ttc aat tac cag caa gga tct ccc act tgg ttg gct cat gga act tta<br>Phe Asn Tyr Gln Gln Gly Ser Pro Thr Trp Leu Ala His Gly Thr Leu<br>                  475                      480                      485 | 1613 |
| ctt tct tgg tat tgg aat tca ttg atg ttc cct tgg gat tat gat att<br>Leu Ser Trp Tyr Trp Asn Ser Leu Met Phe Pro Trp Asp Tyr Asp Ile<br>490                             495                      500 | 1661 |
| gat gtg caa atg cca atc aag agt ttg aac aat cta tgt gct aac ttc<br>Asp Val Gln Met Pro Ile Lys Ser Leu Asn Asn Leu Cys Ala Asn Phe<br>505                             510                      515                      520 | 1709 |
| aac caa tca tta ata att gag gat ctt act gaa gga tat tct tct ttt<br>Asn Gln Ser Leu Ile Ile Glu Asp Leu Thr Glu Gly Tyr Ser Ser Phe<br>                  525                      530                      535 | 1757 |
| ttc ttg gat tgc gga tca agt atc acg cat aga aca aaa ggc aaa gga | 1805 |

```
        Phe Leu Asp Cys Gly Ser Ser Ile Thr His Arg Thr Lys Gly Lys Gly
                        540                 545                 550 tta aac ttc att gat gca aga ttc ata aat gtt gaa aca ggc ctt tat        1853
Leu Asn Phe Ile Asp Ala Arg Phe Ile Asn Val Glu Thr Gly Leu Tyr
                555                 560                 565 atc gat atc act gga tta agt acc agt cag tca gct cga ccg cca agg        1901
Ile Asp Ile Thr Gly Leu Ser Thr Ser Gln Ser Ala Arg Pro Pro Arg
            570                 575                 580 ttt agt aac gct tcg aag aaa gat cct att tac aat tgc agg aat aat        1949
Phe Ser Asn Ala Ser Lys Lys Asp Pro Ile Tyr Asn Cys Arg Asn Asn
585                 590                 595                 600 cat ttc tac tct cat aac aat ata gca cct ctc aaa tac acg ttg atg        1997
His Phe Tyr Ser His Asn Asn Ile Ala Pro Leu Lys Tyr Thr Leu Met
                605                 610                 615 gag ggg gtt ccc agt ttc att cct caa cag tat gaa gaa ata ttg aga        2045
Glu Gly Val Pro Ser Phe Ile Pro Gln Gln Tyr Glu Glu Ile Leu Arg
            620                 625                 630 gag gag tat aca act ggt ttg act tcg aaa cac tac aac ggc aac ttt        2093
Glu Glu Tyr Thr Thr Gly Leu Thr Ser Lys His Tyr Asn Gly Asn Phe
        635                 640                 645 ttt atg act caa ttg aat ttg tgg ctt gaa aga gat cca atg cta gca        2141
Phe Met Thr Gln Leu Asn Leu Trp Leu Glu Arg Asp Pro Met Leu Ala
650                 655                 660 ctt gtg cct tca tcc aaa tac gaa att gaa ggt gga ggg gtg gac cat        2189
Leu Val Pro Ser Ser Lys Tyr Glu Ile Glu Gly Gly Gly Val Asp His
665                 670                 675                 680 aac aag att atc aag tct att ctt gaa ctt tcc aac atc aaa aaa ttg        2237
Asn Lys Ile Ile Lys Ser Ile Leu Glu Leu Ser Asn Ile Lys Lys Leu
                685                 690                 695 gaa ttg ttg gat gat aat ccc gat ata tta gag gag gtg atc agg aca        2285
Glu Leu Leu Asp Asp Asn Pro Asp Ile Leu Glu Glu Val Ile Arg Thr
            700                 705                 710 tac gaa ctg act tcc att cac cat aaa gag atg cag tat ctt tcc agt        2333
Tyr Glu Leu Thr Ser Ile His His Lys Glu Met Gln Tyr Leu Ser Ser
        715                 720                 725 gtc aaa cca gat ggg gac agg tcc atg cag tca aat gac ata acc agt        2381
Val Lys Pro Asp Gly Asp Arg Ser Met Gln Ser Asn Asp Ile Thr Ser
    730                 735                 740 tct tac cag gag ttt cta gca agt ctg aag aaa ttc cag cct tta cgc        2429
Ser Tyr Gln Glu Phe Leu Ala Ser Leu Lys Lys Phe Gln Pro Leu Arg
745                 750                 755                 760 aaa gat ttg ttc caa ttt gag cgg ata gac ctt tct aag cat aga aaa        2477
Lys Asp Leu Phe Gln Phe Glu Arg Ile Asp Leu Ser Lys His Arg Lys
                765                 770                 775 cag tga gcagccgttt tgcctaaaat gttccagaaa ctataggata aatatataca        2533
Gln gtaatgaatt aggtgatgtt agcatttagt ccccaaaaat acctcgaatc tccagctcca        2593
tagcgcaaaa tctccaaatc tacttcaaga cgcactcat                                2632

<210> SEQ ID NO 3
<211> LENGTH: 777
<212> TYPE: PRT
<213> ORGANISM: Pichia pastoris

<400> SEQUENCE: 3

Met Thr Leu Arg Ser Ala Ile Lys Ala Arg Thr Ser Lys Gly Leu Ile
1               5                   10                  15

Gly Ala Val Ile Ile Ala Ser Ile Ile Phe Phe Thr Thr Val Thr Phe
            20                  25                  30
```

-continued

```
Tyr Asp Glu Ser Lys Ile Val Gly Ile Ile Arg Val Ser Asp Thr Tyr
         35                  40                  45

Thr Gly His Ser Ala Val Ser Ser Thr Phe Asn Ala Ser Ser Val Val
         50                  55                  60

Ser Asp Asn Lys Ile Asn Gly Tyr Gly Leu Pro Leu Ile Asp Thr Glu
 65                  70                  75                  80

Ser Asn Ser Arg Tyr Glu Asp Pro Asp Ile Ser Ile Glu Asn Glu
                 85                  90                  95

Leu Arg Tyr Arg Ile Ala Gln Ser Thr Lys Glu Glu Asn Met Trp
             100                 105                 110

Lys Leu Asp Thr Thr Leu Thr Glu Ala Ser Leu Lys Ile Pro Asn Ile
             115                 120                 125

Gln Ser Phe Glu Leu Gln Pro Phe Lys Glu Arg Leu Asp Asn Ser Leu
         130                 135                 140

Tyr Asn Ser Lys Asn Ile Gly Asn Phe Tyr Phe Tyr Asp Pro Arg Leu
145                 150                 155                 160

Thr Phe Ser Val Tyr Leu Lys Tyr Ile Lys Asp Lys Leu Ala Ser Gly
                 165                 170                 175

Ser Thr Thr Asn Leu Thr Ile Pro Phe Asn Trp Ala His Phe Arg Asp
             180                 185                 190

Leu Ser Ser Leu Asn Pro Tyr Leu Asp Ile Lys Gln Glu Asp Lys Val
         195                 200                 205

Ala Cys Asp Tyr Phe Tyr Glu Ser Ser Asn Lys Asp Lys Arg Lys Pro
    210                 215                 220

Thr Gly Asn Cys Ile Glu Phe Lys Asp Val Arg Asp Glu His Leu Ile
225                 230                 235                 240

Gln Tyr Gly Ile Ser Ser Lys Asp His Leu Pro Gly Pro Phe Ile Leu
                 245                 250                 255

Lys Ser Leu Gly Ile Pro Met Gln His Thr Ala Lys Arg Leu Glu Ser
             260                 265                 270

Asn Leu Tyr Leu Leu Thr Gly Ala Pro Val Pro Leu Ser Leu Ser Phe
         275                 280                 285

Met Thr Lys Lys Gly Leu Tyr Gln Val Gly Val Asp Gln Thr Gly Lys
    290                 295                 300

Leu Asp Pro Asn Ile Ala Arg Thr Glu Leu Trp Glu Phe Tyr Lys Asn
305                 310                 315                 320

Gly Lys Glu Asn Leu Gln Phe Asn Ala Gln Glu Glu Leu Ser His Leu
                 325                 330                 335

Ile Glu Thr Val Pro Ser Ser Asn Ser Ser Gly Glu Gly Tyr
             340                 345                 350

Phe Thr Thr Glu Leu Lys Glu Asn Asn Phe Glu Leu Pro Leu Ser Lys
         355                 360                 365

Asn Asp Phe Thr Phe Asp Ser Glu Val Glu Ser Leu Ile Lys Gly
    370                 375                 380

Leu Ser Glu Gln Asp Leu Asp Leu His Thr Gln Arg Tyr Lys Glu Ser
385                 390                 395                 400

Leu Gln Tyr Ser Phe Ala Thr Arg Glu Asn Asp Val Lys Lys Tyr Phe
                 405                 410                 415

Tyr Glu Ala Arg Met Ile Ile Asn Thr Val Asn Lys Glu Gly Gly Ala
             420                 425                 430

His Tyr Asp Trp Arg Phe Phe Asn Gly Ala Met Asn His Glu Ser Ser
         435                 440                 445
```

-continued

```
Gly Phe Thr Glu Glu Arg Gln Leu Arg Lys Arg Ser Val Leu His
    450                 455                 460

Arg Leu Leu Arg Asn Trp Leu Val Phe Asn Tyr Gln Gln Gly Ser Pro
465                 470                 475                 480

Thr Trp Leu Ala His Gly Thr Leu Leu Ser Trp Tyr Trp Asn Ser Leu
                485                 490                 495

Met Phe Pro Trp Asp Tyr Asp Ile Asp Val Gln Met Pro Ile Lys Ser
                500                 505                 510

Leu Asn Asn Leu Cys Ala Asn Phe Asn Gln Ser Leu Ile Ile Glu Asp
                515                 520                 525

Leu Thr Glu Gly Tyr Ser Ser Phe Phe Leu Asp Cys Gly Ser Ser Ile
    530                 535                 540

Thr His Arg Thr Lys Gly Lys Gly Leu Asn Phe Ile Asp Ala Arg Phe
545                 550                 555                 560

Ile Asn Val Glu Thr Gly Leu Tyr Ile Asp Ile Thr Gly Leu Ser Thr
                565                 570                 575

Ser Gln Ser Ala Arg Pro Pro Arg Phe Ser Asn Ala Ser Lys Lys Asp
                580                 585                 590

Pro Ile Tyr Asn Cys Arg Asn Asn His Phe Tyr Ser His Asn Asn Ile
                595                 600                 605

Ala Pro Leu Lys Tyr Thr Leu Met Glu Gly Val Pro Ser Phe Ile Pro
    610                 615                 620

Gln Gln Tyr Glu Glu Ile Leu Arg Glu Tyr Thr Thr Gly Leu Thr
625                 630                 635                 640

Ser Lys His Tyr Asn Gly Asn Phe Phe Met Thr Gln Leu Asn Leu Trp
                645                 650                 655

Leu Glu Arg Asp Pro Met Leu Ala Leu Val Pro Ser Ser Lys Tyr Glu
                660                 665                 670

Ile Glu Gly Gly Gly Val Asp His Asn Lys Ile Ile Lys Ser Ile Leu
    675                 680                 685

Glu Leu Ser Asn Ile Lys Lys Leu Glu Leu Leu Asp Asp Asn Pro Asp
    690                 695                 700

Ile Leu Glu Glu Val Ile Arg Thr Tyr Glu Leu Thr Ser Ile His His
705                 710                 715                 720

Lys Glu Met Gln Tyr Leu Ser Ser Val Lys Pro Asp Gly Asp Arg Ser
                725                 730                 735

Met Gln Ser Asn Asp Ile Thr Ser Ser Tyr Gln Glu Phe Leu Ala Ser
                740                 745                 750

Leu Lys Lys Phe Gln Pro Leu Arg Lys Asp Leu Phe Gln Phe Glu Arg
    755                 760                 765

Ile Asp Leu Ser Lys His Arg Lys Gln
    770                 775

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 4
ccgaccctcg tctcacgtgg tcc                                          23

<210> SEQ ID NO 5
<211> LENGTH: 29
```

-continued

```
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 5
ccaagcttag actttggtaa ctcttccag                                      29
```

PROCESS FOR PRODUCING PROTEIN WITH REDUCTION OF ACIDIC SUGAR CHAIN AND GLYCOPROTEIN PRODUCED THEREBY

This application claims the benefit of earlier filed International Application No. PCT/JP01/04070 filed May 16, 2001.

TECHNICAL FIELD

The present invention relates to the control of the addition of mannose phosphate to a sugar chain in the production of heterologous glycoprotein using yeast. More particularly, the invention relates to the control of an acidic sugar chain-forming function in the core-like sugar chain of the glycoprotein contained in a yeast belonging to the genus *Pichia*. The present invention also relates to a gene participating in the addition of mannose phosphate to a sugar chain, a mutant gene thereof, a vector carrying the mutant gene, a transformant having been transformed by the vector, a method for producing a protein with reduction of acidic sugar chain using a means for controlling the gene, and a protein with reduction of acidic sugar chain prepared by the method. In addition, the invention relates to a protein encoded by the above gene and an antibody recognizing the protein.

BACKGROUND ART

Production using a genetically modified microorganism is advantageous over the production using mammalian cells with respect to several points including the low production cost and high culture technique that has been accumulated as the fermentation technology. Recently, attention has been paid to a methylotrophic yeast belonging to the genus *Pichia* (e.g., *Pichia pastoris*) as an effective host for producing a heterologous protein [Cregg, J. M. et al., Bio/Technology 11, 905 (1993)]. Yeasts belonging to the genus *Pichia* have much larger secretary expression amounts than *Saccharomyces cerevisiae*, and culture techniques for them are established, so that they are very suitably used as yeasts for industrially producing human serum albumin and so on.

In case a microorganism is used as a host for producing a heterologous glycoprotein, however, it is impossible to add a sugar chain having the structure and composition same as human glycoprotein, and this is a problem. For asparagine-linked sugar chain of glycoprotein derived from mammalian cells including human cells, three types are known, i.e., complex type, hybrid type, and high-mannose type. On the other hand, in prokaryotes such as *Escherichia coli*, the addition per se of sugar chain does not occur.

For asparagine-linked sugar chains added in *Saccharomyces cerevisiae*, only the high mannose type is known. With respect to asparagine-linked sugar chains of glycoprotein in *S. cerevisiae*, ER core-like sugar chain (Man8GlcNAc2) common with that of mammal is added in the endoplasmic reticulum, and in the following process a large amount (30–150 molecules) of mannose is formed as sugar outer chain [Kukuruzinska, M. A. et al., Ann. Rev. Biochem. 56, 915 (1987)]. Therefore, high mannose-type sugar chains having been added to the glycoprotein derived from *S. cerevisiae* contain more amount of mannose than that of a mammalian cell, i.e., they contain mainly hypermannosylated sugar chains.

The α-1,3 linkage in mannose of the sugar chain of *S. cerevisiae* is not found in sugar chains of mammalian including human being. Therefore, it is considered that this structure might exhibit an antigenic property to human beings [Ballou. C. E., Methods Enzymol., 185, 440–470 (1990)]. In addition, the fact that sugar chains are involved in various in vivo roles such as the blood clearance, the maintenance of protein structural, the contribution to activity, and the localization [Takeuchi, Tanpakushitsu Kakusan Kouso, special issue "Glycoconjugate", 37, 1713 (1992)] suggests that a heterologous protein having a high mannose-type sugar chain produced by using *S. cerevisiae* has a big problem in the aspect of function.

Recently, with respect to *S. cerevisiae*, OCH1 gene coding α-1,6-mannosyltransferase that is the key enzyme for the sugar outer chain mannose elongation was cloned [Nakayama, K., EMBO J. 11, 2511 (1992)]. It was reported that in Δoch1-mnn1-double mutant having mutations in both OCH1 gene and MNN1 gene coding a protein having a function of adding mannose to the core-like sugar chain with the α-1,3 linkage, only ER core-like sugar chain common to that of mammal is added [Jigami, Y., Tanpakushitsu Kakusan Kouso, 39, 657 (1994)].

It is known that a mannose-type sugar chain is added in yeasts belonging to the genus *Pichia* in a manner similar to that of *S. cerevisiae*, while it was shown that the mannose addition number of a yeast belonging to the genus *Pichia* is less than that of *S. cerevisiae* and that sugar chain of yeasts belonging to the genus *Pichia* does not contain the α-1,3 linkage that is considered to be highly antigenic to human beings [Trimble, R. B. et al., J. Biol. Chem. 266, 22807 (1991)]. In addition, a gene homologous to OCH1 gene of *S. cerevisiae* was cloned, and it was confirmed that control of the gene in yeast strain belonging to the genus *Pichia* suppresses the elongation of the sugar chain. Therefore, this strain is useful as a host for producing a heterologous glycoprotein having a sugar chain structure similar to the human-type one [Japan Patent Laid Open Hei 9-3097].

Although a technique has been developed which suppresses the elongation of the sugar chain and permits expressing a glycoprotein similar to the ER core-like sugar chain, there remains the following problem also in a yeast belonging to the genus *Pichia*: a heterologous glycoprotein has an antigenicity caused by an acidic sugar chain in case the heterologous glycoprotein produced by using a yeast as a host is administered to human beings as a medicine.

It is known that acidic sugar chain added by mannose-6-phosphate (Man-6-P) to a core-type sugar chain and/or sugar outer chain are/is formed in *S. cerevisiae* [Hernandez, L. M. et al. J. Biol. Chem. 264, 13648–13659 (1989)]. As FIG. 1 illustrates, mannose phosphate is added not only to the sugar outer chain but also to the core-like sugar chain in *S. cerevisiae* [Jigami, Y. and Odani, T., Biochim. Biophys. Acta, 1426, 335–345 (1999)]. This sugar chain containing the phosphate group does not found in human-type sugar chains. Therefore, it is very likely that this has an antigenicity and it is considered that this can be a big problem in case of developing a medicine. With respect to *S. cerevisiae*, MNN4 gene and MNN6 gene have been cloned and analyzed as genes participating in the transfer of mannose phosphate [Odani, T. et al. Glycobiology 6, 805 (1996); Wang, X.-H., et al. J. Biol. Chem., 272, 18117 (1997)]. It was confirmed in vitro that the transfer of mannose phosphate to the core-like sugar chain or Man5GlcNAc2 depends on Mnn6p (protein encoded by MNN6). Therefore, it is assumed that the MNN6 gene codes the main body of mannose phosphate transferase.

In addition, with respect to MNN4 gene, the mannose phosphate-transferring activity is suppressed in mnn4 mutant, and phosphate content is increased by the overexpression. Therefore, MNN4 gene is considered to be a factor that positively controls Mnn6 protein. It was elucidated that the transfer of phosphate to a sugar chain is decreased in yeast whose MNN4 gene was disrupted by a genetic engineering technique [Japan Patent Laid Open Hei 9-266792]. Therefore, the yeast can be used for producing a glycoprotein having a reduced antigenicity to human beings. However, even if S. cerevisiae MNN4 gene-controlled strain is used, the acidic sugar chain in the core-like sugar chain cannot be sufficiently suppressed, with less than 30% of the whole sugar chain being an acidic sugar chain [Odani T. el al., Glycobiology 6, 805–810 (1996); Japan Patent Laid Open Hei 9-266792].

On the other hand, with respect to yeasts belonging to the genus Pichia, only a few reports have been published concerning the phosphorylated sugar chain of a heterologous protein so far. For example, in kringle 2 domain of the tissue plasminogen activator, a mannose phosphate group had been transferred to 20% of the sugar chain of Man10-14GlcNAc2 [Miele, R. G. et al. Biotechnol. Appl. Biochem. 26, 79 (1997)]. In addition, although mannose phosphate group was detected in the sugar chain of Man9- 14GlcNAc2 of aspartic protease, a phosphorylated sugar chain was not detected in five other heterologous proteins investigated at the same time [Montesino, R. et al. Protein Exp. Purif. 14, 197 (1998)]. Therefore, with respect to a yeast belonging to the genus Pichia, the frequency of the transfer of mannose phosphate to a sugar chain might be low, but phosphorylated sugar chains are detected in some heterologous proteins produced thereby. Therefore, it would be desirable to suppress the addition of mannose phosphate to the sugar chain in case administered to human beings as a medicine.

Although the expression system using a yeast belonging to the genus Pichia as a host is effective for the industrial production because of its high productivity, the mechanism of the transfer of mannose phosphate to the sugar chain of a glycoprotein originally possessed or produced, as a heterologous protein, by a yeast belonging to the genus Pichia has been studied only insufficiently. Therefore, with respect to a yeast belonging to the genus Pichia, the mechanism of the transfer of mannose phosphate to a glycoprotein sugar chain is quite unknown, and it is an important subject from the viewpoint of avoiding the antigenicity in the development of a medicine for administering to human beings or mammalians to suppress the transfer of mannose phosphate in a glycoprotein-expressing system in which yeast belonging to the genus Pichia is used as a host.

Thus, the purposes of the present invention are to find a gene participating in the addition of mannose phosphate to the sugar chain of a glycoprotein derived from a yeast belonging to the genus Pichia and to provide a means for controlling the addition. Other purposes of the present invention are to provide a method for producing a protein whose acidic sugar chain was reduced using a yeast strain belonging to the genus Pichia in which the gene is controlled and to provide a glycoprotein produced by the method.

The applicants' zealous examinations for solving these problems resulted in the success of the cloning of the gene coding a protein that is originated from a yeast belonging to the genus Pichia and participates in the addition of mannose phosphate, the finding that the protein participates in the addition of mannose phosphate in an expression system using a yeast belonging to the genus Pichia as a host, and the confirmation that acidic sugar chain of the glycoprotein produced by using the gene-controlled strain is remarkably reduced, and consequently reached the completion of the present invention.

DISCLOSURE OF THE INVENTION

The present invention relates to a method for controlling the formation of the acidic sugar chain in a yeast belonging to the genus Pichia wherein a gene participating in the formation of the acidic sugar chain in the core-like sugar chain of at least a glycoprotein derived from the chromosomal gene of a wild-type yeast strain belonging to the genus Pichia is controlled, a polynucleotide containing the base sequence shown by the nucleotides from the 150th to the 2480th of the base sequence of SEQ ID NO:2 in the sequence listing coding a protein participating in the formation of an acidic sugar chain in the core-like sugar chain derived from a yeast belonging to the genus Pichia, a polynucleotide having a reduced function by inducing mutation(s) to the polynucleotide, a recombinant vector carrying the polynucleotide having a reduced function, a method for producing a glycoprotein using the above controlling method or the above transformant in the production of a heterologous glycoprotein by the genetic engineering technique using a yeast belonging to the genus Pichia as a host, a glycoprotein produced by the method for producing a glycoprotein, a protein containing the amino acid sequence of SEQ ID NO:3 in the sequence listing, and an antibody specifically recognizing the protein.

The present invention will be described in detail below.

Figure 1:
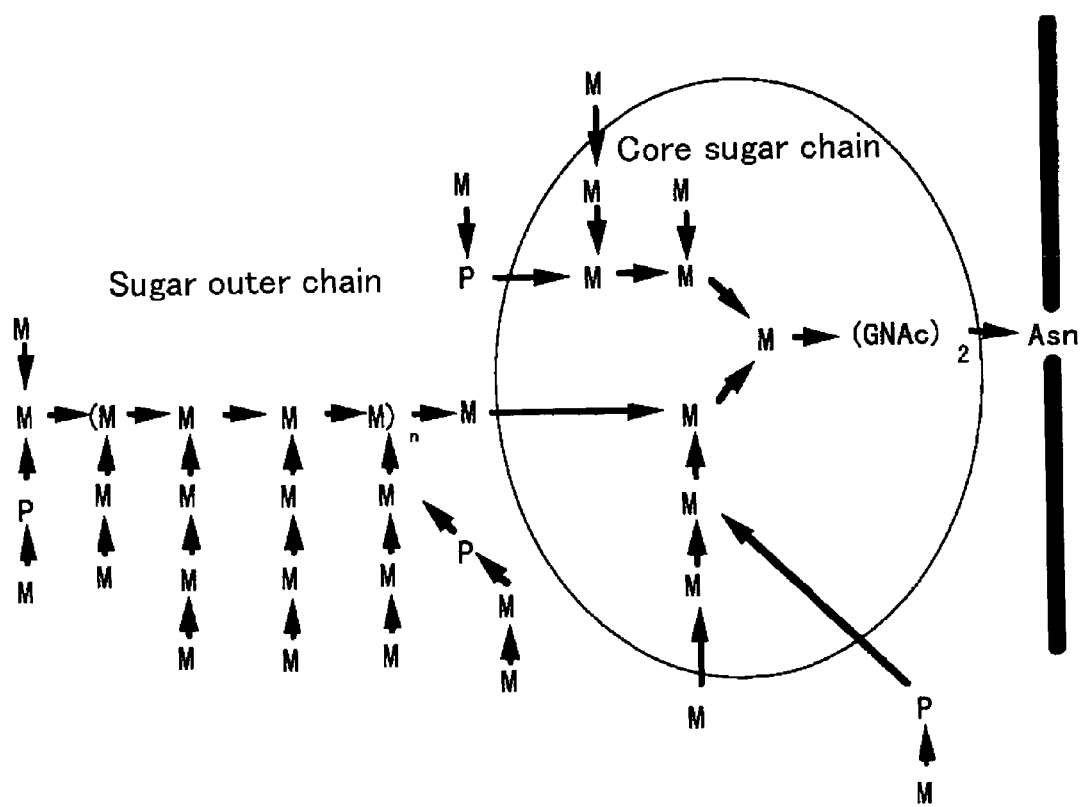
FIG. 1 illustrates the structure of an asparagine-linked sugar chain of S. cerevisiae (symbols: Asn, asparagine; GNAc, N-acetyl glucosamine; M, mannose; P, phosphate) (partially modified from FIG. 1 in Jigami, Y. and Odani, T., Biochim. Biophys. Acta, 1426, 335–345 (1999)).

(A) A neutral sugar chain of recombinant ATIII derived from strain RH101

(B) A neutral sugar chain of recombinant ATIII derived from strain 9G4

(C) An acidic sugar chain of recombinant ATIII derived from strain RH101

(D) An acidic sugar chain of recombinant ATIII derived from strain 9G4

FIG. 10 illustrates the evaluation by ELISA of the inhibition by human ATIII derived from plasma in the binding reaction of immobilized recombinant human ATIII derived from a wild-type yeast belonging to the genus *Pichia* or recombinant human ATIII derived from a PNO1 gene-controlled strain with anti-serum against recombinant human ATIII derived from a wild-type yeast belonging to the genus *Pichia* or anti-serum against recombinant human ATIII (derived from a PNO1 gene-controlled strain).

(1) Protein Participating in Formation of Acidic Sugar Chain

The protein participating in the formation of an acidic sugar chain according to the present invention is that produced by a yeast belonging to the genus *Pichia* and has a function for addition of mannose phosphate to a sugar chain of a glycoprotein, particularly for addition of mannose phosphate involved in the core-like sugar chain. A sugar chain having mannose phosphate is an acidic sugar chain. Yeasts belonging to the genus *Pichia* according to the present invention from which a protein participating in the formation of the acidic sugar chain is derived include, for example, *Pichia pastris*, *Pichia finlandica*, *Pichia trehalophila*, *Pichia koclamae*, *Pichia membranaefaciens*, *Pichia methanolica*, *Pichia opuntiae*, *Pichia thermotolerans*, *Pichia salictaria*, *Pichia guercum*, *Pichia pijperi*, and other yeasts, but not limited thereto. *Pichia pastoris* (called *P. pastoris* hereafter) is preferably used among these.

A protein participating in the formation of an acidic sugar chain according to the present invention can be any protein that is originally derived from a yeast belonging to the genus *Pichia*, and has a function described above. It is preferably a protein having the amino acid sequence of SEQ ID NO: 1 in the sequence listing in its N-terminal region, more preferably a protein substantially containing the amino acid sequence of SEQ ID NO: 3 in the sequence listing.

Such amino acid sequence can be modified in part by substituting, deleting, inserting, and/or adding one or more amino acid moiety or peptide chain as long as the above property is not changed. A protein according to the present invention can be a protein that has a homology of 70% or more to the amino acid of the protein containing the amino acid sequence of SEQ ID NO: 3 in the sequence listing and has an activity of forming an acidic sugar chain in the core-like sugar chain of a glycoprotein produced by a yeast belonging to the genus *Pichia*.

The present invention also claims a polypeptide having a sequence consisting of five consecutive amino acids or more selected from the amino acid sequence of SEQ ID NO: 3 in the sequence listing and an antibody immunologically recognizing the above protein. The polypeptide is useful as an antigen for obtaining an antibody specifically recognizing the above protein.

The protein participating in the formation of an acidic sugar chain according to the present invention can be produced by culturing a yeast belonging to the genus *Pichia* according to the conventional method, preferably under a condition suitable for the proliferation of the yeast, followed by extracting/purifying according to the conventional method from the obtained cells. The polypeptide can be synthesized based on the amino acid sequence exemplified in the present invention or can be produced by the conventional recombinant DNA technique based on the base sequence exemplified in the present invention. The antibody such as polyclonal antibody or monoclonal antibody can be produced by well-known methods for producing antibodies. The above polypeptide thus prepared and an antibody recognizing the above protein, are useful for obtaining a means for controlling the expression of an acidic glycoprotein in a glycoprotein expression system using a yeast belonging to the genus *Pichia* as a host, for example, for purifying and obtaining a protein participating in the formation of an acidic sugar chain according to the present invention. For making the following description easy, the protein consisting of the amino acid sequence of SEQ ID NO: 3 in the sequence listing of the present invention may be called 'Pno1 protein', and the gene coding the protein is called 'PNO1 gene'.

(2) Gene Coding Pno1 Protein

The gene participating in the formation of an acidic sugar chain according to the present invention is characterized by having a base sequence coding Pno1 protein derived from a yeast belonging to the genus *Pichia* according to the present invention described above. Such a base sequence is, for example, a base sequence coding the amino acid sequence of SEQ ID NO: 3 in the sequence listing, more preferably a polynucleotide substantially from the 150th base to the 2480th base of the base sequence of SEQ ID NO: 2 in the sequence listing, although any base sequence that can code Pno1 protein according to the present invention can be used. Such a base sequence can be a polynucleotide that contains at least 60 consecutive bases from the 5'-end of the protein coding sequence in the base sequence of SEQ ID NO: 2 in the sequence listing and codes the protein participating in the formation of the acidic sugar chain in a yeast belonging to the genus *Pichia*.

The gene can be produced by well-known methods. For example, at least a part of the DNA or whole DNA can be produced by using a DNA synthesizer based on the base sequence exemplified in the present invention. The gene can also be produced by the amplification with the PCR method using the chromosomal DNA of a yeast belonging to the genus *Pichia* (e.g., *P. pastoris*).

The gene participating in the formation of an acidic sugar chain according to the preset invention is provided as a gene coding Pno1 protein produced by a yeast belonging to the genus *Pichia* first by the present invention. Therefore, the gene participating in the formation of an acidic sugar chain according to the present invention is very useful in elucidating the mechanism of transfer of the mannose phosphate having been added to a sugar chain of a glycoprotein in a glycoprotein-expressing system using a yeast belonging to the genus *Pichia* as a host.

Pno1 protein according to the present invention has a function of transferring mannose phosphate to a sugar chain of a glycoprotein produced by using a yeast belonging to the genus *Pichia* as a host, and it is more antigenic against human beings compared with a glycoprotein derived from a mammalian cell. Therefore, the elucidation of PNO1 gene according to the present invention would permit, in the future, providing a method for reducing or removing in a gene level a mannose phosphate-transferring activity originally possessed by a yeast belonging to the genus *Pichia* for expressing/producing, using a yeast belonging to the genus *Pichia* as a host, a pharmaceutically useful heterologous glycoprotein to which a mannose phosphate group is not added. To reduce or remove the mannose phosphate-transferring activity originally possessed by Pno1 protein according to the present invention can be achieved by modifying the PNO1 gene according to the present invention so as to at least suppress the production of a functional product encoded by the DNA.

(3) Transformant in which Function of PNO1 Gene is Suppressed

To the transformant according to the present invention, one of methods is applied that permits suppressing the expression of PNO1 gene or making the transformant express a product having an attenuated function compared with a native functional product to reduce or remove the mannose phosphate-transferring activity originally possessed by Pno1 protein according to the present invention. The methods include, for example, a method in which a polynucleotide derived from PNO1 gene is transformed using a recombinant vector carrying a polynucleotide modified so as to at least suppress the production of a functional product encoded by the gene, and a method in which the translation/expression of a functional product encoded by the gene is suppressed by using the antisense oligonucleotide against the gene.

(3-1) PNO1 Gene-Disrupted Yeast Strain (PNO1 Disruptant)

PNO 1 disruptant according to the present invention is a yeast belonging to the genus *Pichia* having a suppressed ability of transferring mannose phosphate in the core-like sugar chain of a glycoprotein compared with a wild-type yeast strain belonging to the genus *Pichia* based on having a modified PNO1 gene.

The 'modified PNO1 gene' is a gene in which a part of the base sequence of the DNA coding a protein participating in the transfer of mannose phosphate to the core-like sugar chain of a glycoprotein derived from a yeast belonging to the genus *Pichia* is modified so as to at least suppress the production of a functional product encoded by the DNA.

'To at least suppress the production of a functional product' means not only the case in which PNO1 gene is not expressed and no native-type Pno1 protein according to the present invention is produced, but also the case in which a product obtained, even if it is expressed, is not identical to Pno1 protein according to the present invention and the function is attenuated (i.e., the case in which the product has no mannose phosphate-transferring activity possessed by native-type Pno1 protein and the case in which the product has a lower mannose phosphate-transferring activity than that of the native Pno1 protein).

The 'wild-type yeast strain belonging to the genus *Pichia*' means a yeast strain belonging to the genus *Pichia* that has the native-type PNO1 gene and keeps the original mannose phosphate-transferring activity.

Therefore, any embodiments for modifying a gene can be used as long as the embodiment makes the expression of the gene impossible or reduces the expression, or a product expressed using modified PNO1 gene has no mannose phosphate-transferring activity in the core-like sugar chain originally possessed by a product of native-type PNO1 gene, or a product has an reduced one compared with the mannose phosphate-transferring activity in the core-like sugar chain originally possessed by the product of native-type PNO1 gene even if it does.

The embodiments include, for example, a modification in which at least one nucleotide is deleted from or inserted into the DNA base sequence of PNO1 gene and PNO1 promoter region and a modification in which at least one nucleotide is substituted in the base sequence in native-type PNO1 gene and PNO1 promoter region. 'PNO1 promoter region' means a DNA regulating the expression of PNO1 gene in 5'-side of PNO1 gene. The embodiments also include a modification in which at least one nucleotide in base sequences of the native-type PNO1 gene and the PNO1 promoter region is added. Such modification moves the reading frame, modifies the base sequence, or reduces the promoter activity, so that the product might not be expressed or expressed in a reduced amount even if expressed, or the function of the product obtained might become different from that of a product derived from a native-type DNA.

Suitable modification methods include a method in which a marker gene for a transformation is inserted in the coding region of the native-type PNO1 gene. This method advantageously permits disrupting the native-type PNO1 gene and easily screening a mutant having the modified PNO1 gene by using the introduced marker gene as an index. It is also possible to insert a gene coding a glycoprotein to produce in addition to the transformation marker gene. This permits modifying the PNO1 gene and expressing the glycoprotein to produce simultaneously in one operation.

Transformation marker genes for the present invention include HIS4 gene, ARG4 gene, URA3 gene, SUC2 gene, ADE1 gene, ADE2 gene, G418 resistant gene, Zeocin resistance gene, and so on, of *P. pastoris* or *Saccharomyces cerevisiae*.

Regarding with the genes of glycoprotein, any DNA coding desired glycoproteins to produce can be used for the present invention. They include anti-thrombin III (ATIII) gene, fibrinogen gene, heparin cofactor II gene, antibody gene, urokinase gene, interferon α gene, chymase gene, urinary trypsin inhibitor gene, and so on.

A PNO1 disruptant according to the present invention can be prepared by various methods. Those methods include the modification of the native-type PNO1 gene in a wild-type yeast belonging to the genus *Pichia* or the introduction of random mutation into a wild-type yeast belonging to the genus *Pichia* followed by the selection of a mutant showing the suppressed transfer of mannose phosphate compared with a wild-type yeast belonging to the genus *Pichia*. The modification of the native-type PNO1 gene in a wild-type yeast belonging to the genus *Pichia* is preferably used.

The method for preparing a modified yeast strain belonging to the genus *Pichia* by modifying the native-type PNO1 gene can be carried out, concretely, by introducing DNA to be transduced into a specific position of the native-type PNO1 gene by the site-specific integration method. A transduced DNA is integrated by replacing with the intrinsic native-type DNA of a host. A suitable method for introducing DNA to be transduced into a target position of a yeast host is to prepare a linear DNA fragment in which the inside of the target gene DNA fragment is deleted or a selection marker gene DNA or a gene expression DNA fragment coding a glycoprotein is inserted. Thus, direction is given so as to cause the homologous recombination in a specific site of a DNA whose expression product affects the mannose phosphate-transferring activity by the transformation.

(3-2) Yeast Strain Belonging to Genus *Pichia* into which Antisense Oligonucleotide of PNO1 Gene was Imported In order to at least suppress the production of a functional product encoded by PNO1 gene, it is also possible to construct an antisense oligonucleotide against PNO1 gene to use a wild-type yeast strain belonging to the genus *Pichia* into which the antisense oligonucleotide was imported. In a wild-type yeast belonging to the genus *Pichia* into which an antisense oligonucleotide against PNO1 gene was imported, the transcription of mRNA from PNO1 gene, the transfer of the transcripted mRNA from the nucleus to the cytoplasm, and the translation of Pno1 protein are inhibited, so that Pno1 protein is not synthesized. The antisense oligonucleotide against PNO1 gene can be easily synthesized by the well-known DNA-synthesizing method preferably by selecting a base sequence specific to PNO1 gene based on the base sequence of PNO1 gene (SEQ ID NO: 2 in the sequence listing).

The transformation of a wild-type yeast belonging to the genus *Pichia* can be carried out by a usual method adopted in the field such as the spheroplast method [Cregg, J. M. et al. Mol. Cell Biol. 5, 3376 (1985)], the lithium chloride method [Ito, H. et al. J. Bacteriol. 153, 163 (1983)], the electroporation method [Scorer, C. A. et al. J. Bio/technology 12, 181 (1994)], and so on.

Although any host cells derived from wild-type yeast belonging to the genus *Pichia* can be used for the transformation, methylotrophic yeasts that can efficiently use methanol as the sole carbon and energy sources are preferably used. Suitable methylotrophic yeasts include auxotrophic *P. pastoris* strain GTS115 (NRRL Y-15851) (his4), *P. pastoris* strain GS190 (NRRL Y-18014) (his4, ura3), *P. pastoris* strain PPF1 (NRRL Y-18017) (his4, arg4), *P. pastoris* strain KM71 (Invitrogen Co.) (his4, aox1::ARG4, arg4), *P. pastoris* strain KM71H (Invitrogen Co.) (aox1::ARG4, arg4), *P. pastoris* strain SMD1168 (Invitrogen Co.) (his4, pep4), *P. pastoris* strain SMD1168H (Invitrogen Co.) (pep4), *P. methanolica* strain PMAD11 (Invitrogen Co.) (ade2-1), *P. methanolica* strain PMAD16 (Invitrogen Co.) (ade2-11, pep4D, prb1D), wild-type *P. pastoris* (NRRL Y-11430, NRRL Y-11431, X-33), and derivatives thereof.

In case the host cell is a strain that lacks at least one auxotrophic marker gene was deleted, it is preferable to use a DNA having the auxotrophic marker gene that is deleted from the host cell for the transduction. Such a method has advantages because a transformant (modified yeast strain belonging to the genus *Pichia*) whose PNO1 gene was modified by integrating a DNA for transduction can be rapidly and simply identified and selected. With respect also to a strain from which any auxotrophic marker gene is not deleted, a modified yeast strain belonging to the genus *Pichia* can be easily obtained by using a drug resistance gene such as G418 resistance gene and Zeocin resistance gene as a selection marker gene.

More preferably, using a sugar chain elongation gene-controlled strain [Japan Patent Laid Open Hei 9-3097] as a host is effective because a protein to which the same core-like sugar chain as the mammalian glycoprotein was added can be produced. Moreover, using a strain having reduced acidic sugar chain in sugar outer chain as a host, which is obtained by inducing mutations by the treatment using a mutagen such as ethane methylsulfonic acid and the like or the exposure to radiation or ultraviolet light and so on, followed by selecting a mutant less stained by Alcian Blue [Ballow, C. E., Methods in Enzymology, 185, 440–470 (1990)], would permit further suppressing the transfer of mannose phosphate having been added to the core-like sugar chain, so that it would be very effective.

(4) Method for Producing Protein Having Reduced Acidic Sugar Chain Using PNO1 GENE-Controlled Yeast Strain An expression system useful for producing a glycoprotein can be prepared by various methods including the method for the introduction of a DNA coding the glycoprotein into the above-mentioned modified yeast strain belonging to the genus *Pichia*, the method for the transformation of a wild-type yeast belonging to the genus *Pichia* by using the DNA prepared by inserting a DNA coding a marker gene and a DNA coding the glycoprotein into native-type PNO1 gene, the method for the subsequently mutation of a native-type PNO1 gene possessed by a recombinant yeast strain belonging to the genus *Pichia* having a DNA coding the glycoprotein to the embodiment of the modified PNO1 gene according to the present invention, and the method for the simultaneous transformation of a wild-type yeast belonging to the genus *Pichia* using the above modified PNO1 gene and a DNA coding a glycoprotein.

The yeast belonging to the genus *Pichia* for expressing a recombinant glycoprotein has, to the reading-frame direction for transcription, at least 1) a promoter region, 2) a DNA coding a substantially desired glycoprotein, and 3) a transcription terminator region. These DNAs are arranged so that a DNA coding a desired glycoprotein can be transcripted to RNA, i.e., they can be related and function each other.

Although for promoters for the present invention, AOX1 promoter (promoter for the first alcohol oxidase gene) of *P. pastoris*, AOX2 promoter (promoter for the second alcohol oxidase gene) of *P. pastoris*, DAS promoter (promoter for dihydroxyacetone synthase gene) of *P. pastoris*, P40 promoter (promoter for P40 gene) of *P. pastoris*, GAPDH promoter (promoter for glyceraldehyde-3-phosphate dehydrogenase gene) of *P. pastoris*, the promoter for aldehyde dehydrogenase gene of *P. pastoris*, the promoter for folate dehydrogenase gene of *P. pastoris*, AUG1 promoter (promoter for alcohol oxidase gene) of *Pichia methanolica* and the like are used, preferably AOX1 promoter of *P. pastoris* [e.g., Ellis et al. Mol. Cell Biol., 5, 111 (1985), U.S. Pat. No. 4,855,231], more preferably mutant AOX2 promoter modified so as to enhance the expression efficiency [Ohi, H. et al. Mol. Gen. Genet., 243, 489–499 (1994), Japan Patent Laid Open Hei 4-299984, U.S. Pat. No. 5,610,036, EP 506,040], is used for them.

A DNA coding secretion signal sequence can exist before a DNA coding a substantially desired glycoprotein. A recombinant glycoprotein-expressing system having such a DNA allows a glycoprotein to be secreted/produced from the host cell, so that a desired glycoprotein can be easily isolated/purified. For the secretion signal sequence, any DNAs that function in a yeast belonging to the genus *Pichia* can be used including a DNA coding a glycoprotein-related native secretion signal sequence, a DNA coding *Saccharomyces cerevisiae* SUC2 signal sequence, a DNA coding PHO1 signal sequence of a yeast belonging to the genus *Pichia*, a DNA coding PRC1 signal sequence of a yeast belonging to the genus *Pichia*, a DNA coding *Saccharomyces cerevisiae* α-mating factor (αMF) signal sequence, a DNA coding bovine lysozyme C signal sequence, and so on.

Although any DNAs coding a glycoprotein having sugar chain structure on the protein molecule can be used as a DNA coding a substantially desirable glycoprotein, DNAs coding pharmaceutically useful glycoproteins including ATIII, fibrinogen, heparin cofactor II, antibody, urokinase, interferon α, chymase, urinary trypsin inhibitor, and the like, are preferably used.

For a transcription terminator used for the present invention, any transcription terminator having a subsegment providing a transcription termination signal to the transcription from a promoter can be used. It can be the same as or different from the gene for a promoter source, or can be obtained from a gene coding a glycoprotein.

The expression system used for the present invention can further contain a selection marker gene in addition to the above DNA sequence. Selection marker genes used include HIS4 gene, ARG4 gene, URA3 gene, SUC2 gene, ADE1 gene, ADE2 gene, G418 resistance gene, and Zeocin resistance gene of *P. pastoris* or *S. cerevisiae*, and so on.

A yeast strain belonging to the genus *Pichia* transformed so as to have a desired phenotype can produce a glycoprotein by cultivation using a method usually used in this field. Any culture condition can be used as long as suited for proliferation of the yeast belonging to the genus *Pichia* and for production of a desired glycoprotein.

After cultivation, a desired heterologous glycoprotein can be obtained by collecting cells in the case of intercellular production or by collecting the culture supernatant in the case of secretory production, followed by purifying using a well-known method such as the fractionation method, the ion exchange method, the gel filtration method, the hydrophobic interaction chromatography, the affinity column chromatography, and so on. Preferably, a glycoprotein having a more reduced acidic sugar chain can be purified/obtained by fractionating a sugar outer chain-added fraction from a core-like sugar chain-added fraction, followed by collecting the latter one.

(5) Produced Glycoprotein

Proteins produced by using PNO1 gene-controlled yeast strain according to the present invention are those having the sugar chain structure on the protein molecule, and include pharmaceutically useful glycoproteins, for example, ATIII, fibrinogen, heparin cofactor II, antibody, urokinase, interferon α, chymase, urinary trypsin inhibitor and the like, but not limited thereto.

The glycoprotein produced by the present invention is characterized in that the transfer of mannose phosphate of at least the core-like sugar chain is suppressed compared with the glycoprotein derived from a wild-type yeast strain belonging to the genus *Pichia*, to preferably 10% or less of total sugar chain, more preferably 1% or less, by the decrease in the expression amount or function of Pno1 protein of a yeast strain belonging to the genus *Pichia*. The glycoprotein produced by the present invention is characterized in that it has reduced antigenicity against human beings and mammalians because the transfer of mannose phosphate is suppressed at least to the core-like sugar chain in the expressed glycoprotein that has been a misgiving in the glycoprotein produced in the yeast expression system in case it is used as a medicine.

BEST MODE FOR CARRYING OUT THE INVENTION

Although examples are given below to describe the present invention more in detail, the present invention is not limited thereto. Enzymes, reagents, and kits used in the examples of the present invention are commercially available, and can be used according to the conventional methods. Protocols used in the cloning of DNAs, the determination of base sequences, the transformation of host cells, the culture of transformed cells, the purification from the resultant culture products, and the sugar chain analysis, are well known for those skilled in the art or can be obtained from literatures.

EXAMPLE 1

Obtaining a Gene Coding a Mannose Phosphate-Transferring Protein Derived from a Yeast Belonging to the Genus *Pichia*

(1) Amplifying/Obtaining *Saccharomyces cerevisiae* MNN4 Gene by PCR Method

In order to clone a gene that is originated from a yeast belonging to the genus *Pichia* and participates in the addition of phosphate, it was planned to screen a homologous gene using, as a probe, MNN4 gene participating in the transfer of mannose phosphate in *S. cerevisiae*. *S. cerevisiae* MNN4 gene was first obtained by using the PCR method based on the DNA sequence disclosed in the literature [Japan Patent Laid Open Hei 9-266792]. The region used as a probe ranges from the 625th to the 2049th with 'A' of initiation codon ATG being 1st.

Primers shown by the base sequences of SEQ ID NO: 4 or SEQ ID NO: 5 in the sequence listing were synthesized. The primer shown by the base sequences of SEQ ID NO: 5 in the sequence listing has an added HindIII recognition sequence in the end. The chromosomal DNA of *Saccharomyces cerevisiae* strain AH22 (a, leu2 his4 can 1) [Hinnen, A. et al., Proc. Nat. Acad. Sci. USA, 75, 1929 (1978)] was extracted with Nucleon MiY Yeast DNA extraction kit (Amersham Pharmacia) and was amplified by Ex Taq PCR Kit (Takara Shuzo) using primers shown by the base sequence of SEQ ID NO: 4 or SEQ ID NO: 5 in the sequence listing, and it was confirmed that a 1.6 kb DNA fragment was amplified. The obtained DNA was digested with ScaI and HindIII, and the resultant product was electrophoresed on agarose, and a 1.4 kb fragment was isolated/purified by using Gene Clean II (Funakoshi) and was inserted between ScaI and HindIII digestion sites of plasmid vector pUC19 using a DNA ligation kit (Takara Shuzo).

The plasmid thus obtained was named 'pTM002'. It was confirmed that the DNA amplified by using the PCR method to insert into pTM002 is a part of *Saccharomyces cerevisiae* MNN4 gene by determining a part of the base sequence of pTM002 using a DNA sequencer (Pharmacia).

(2) Southern Blotting Analysis Using *Saccharomyces Cerevisiae* MNN4 Gene as a Probe Southern blotting analysis was used to examine whether a region that hybridizes to the DNA being cloned into pTM002 exists in the chromosomal DNA of a yeast belonging to the genus *Pichia* or not. The chromosomal DNA of *P. pastoris* strain GTS115 was extracted with Nucleon MiY Yeast DNA extraction kit (Amersham Pharmacia). The obtained extract was digested with restriction enzymes EcoRI, NotI, SacI, SpeI, XbaI, and XhoI followed by applying to agarose gel electrophoresis. The obtained gel was transferred onto Hybond-N nylon membrane filter after denaturation with an alkali and subsequently neutralization, followed by fixing by UV irradiation. The pre-hybridization was carried out according to the instruction for DIG-ELIZA kit (Boehringer Manheim GmbH).

On the other hand, pTM002 was digested with ScaI and HindIII followed by applying to agarose gel electrophoresis, and a 1.4 kb fragment was isolated using Gene Clean II (Funakoshi). Digoxigenin labeling was carried out according to the instruction for DIG-ELISA DNA labeling kit (Boehringer Mannheim GmbH), and hybridization was carried out using the obtained product as a probe. The resultant hybrid were detected according to the instruction for DIG-ELISA kit after washing twice in 0.5×SSC, 0.1% SDS solution at 42° C. for 15 min. As a result, bands were detected when any of the enzymes was used although they were weak; in particular, one band of 7.5 kb was detected when SpeI was used.

(3) Preparation of Phage Library and Plaque Hybridization

A target fragment was cloned into SpeI site by using λZapII (Stratagene). The λZapII undigested vector (Stratagene) was digested with SpeI, and was treated with alkaline phosphatase (Takara Shuzo). On the other hand, the chromosomal DNA of yeast strain GTS115 belonging to the genus *Pichia* was digested with SpeI followed by applying agarose gel electrophoresis, and the region near 7.5 kb was excised.

The obtained fraction was purified using Gene CleanII (Funakoshi) to ligate with the above λZapII/SpeI fragment, followed by carrying out in vitro packaging with Gigapack-GOLD3 Plus (Stratagene). The resultant sample was absorbed on *Escherichia coli* strain XL-1 Blue MRF' that had been prepared so as to give an $OD_{600}$ value of 0.5, and a titer was assayed on an NZY plate that contains IPTG and X-gal.

The recombinant phage absorbed on *Escherichia coli* strain XL-1 Blue MRF', and was subsequently spread on an NZY plate so as to give an appropriate number of plaques. These plaques were moved to a Hybond-N nylon membrane (Amersham Pharmacia) that had been marked so that the position can be recognized, and was denatured with an alkali followed by neutralization, and was subsequently fixed. The plaque hybridization was carried out according to the instruction for the DIG-ELISA kit (Boehringer Mannheim) using a 1.4 kb fragment as a probe which was obtained by digesting pTM002 with ScaI and HindIII and was labeled with digoxigenin. Washing was carried out twice in 0.5× SSC, 1% SDS solution at 42° C. for 15 min, and the detection was carried out according to the instruction the DIG-ELISA kit. As a result, plaques showing positive reactions were detected.

After the phage was made to amplify, XL-1 Blue MRF' strain and Ex assist helper phage were added to incubate at 37° C. for 15 min. Then LB medium was added to culture overnight. The resultant culture was incubated at 65° C. for 20 min and was centrifuged to give a supernatant, which was added to a suspension of *Escherichia coli* strain SOLR followed by disseminating on an LB plate containing ampicilin. A plasmid DNA was extracted by the Mini-Prep method from a colony of *E. coli* that appeared. Such a plasmid that a 7.5 kb fragment is inserted into pBluescript was selected and named 'pTM004'.

Figure 2:
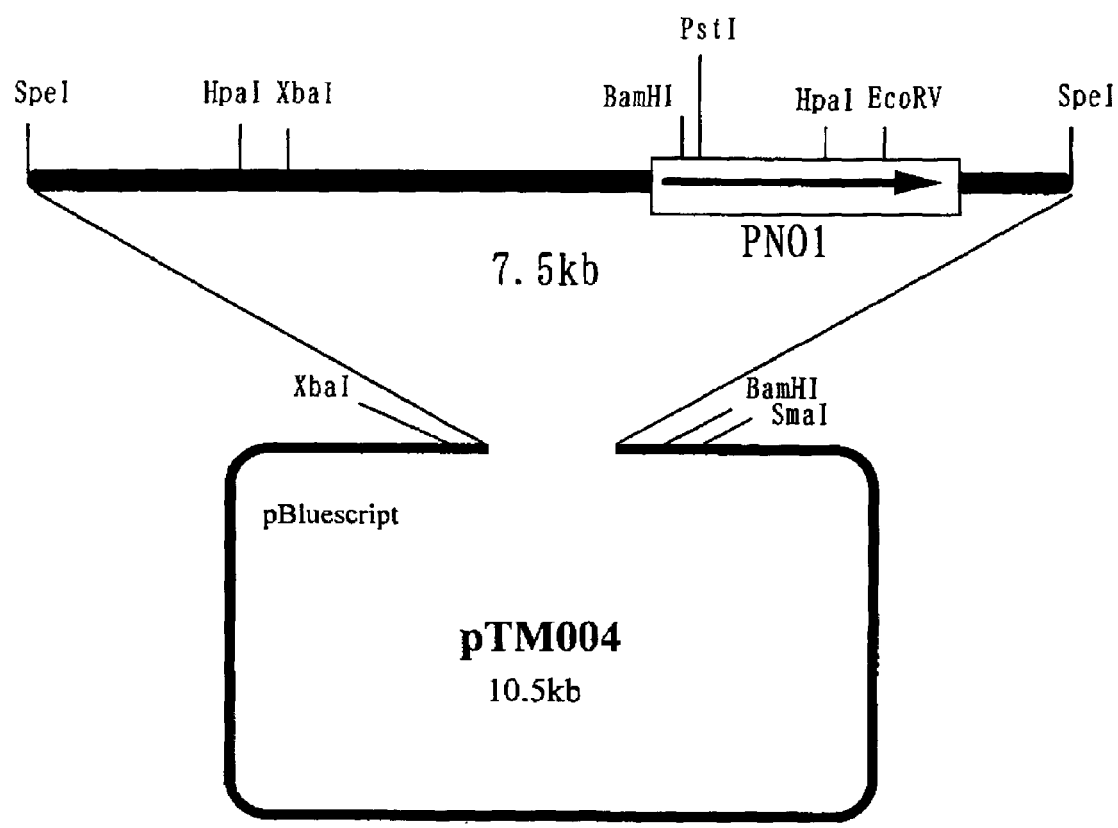
FIG. 2 illustrates plasmid pTM004 into which PNO1 gene of a yeast belonging to the genus Pichia was subcloned.

The restriction enzyme map of pTM004 was prepared as illustrated in FIG. 2. The chromosomal DNA of *P. pastoris* strain GTS115 was digested with EcoRI, NotI, SacI, SpeI, XbaI, and XhoI, and the electrophoresis was carried out on the resultant fragments to prepare two nylon membranes onto which the gel was transferred. Then, southern blotting analyses were carried out in which a SpeI-digested 7.5 kb fragment derived from pTM004 that was purified and labeled with digoxigenin was used as a probe for one membrane and a ScaI and HindIII-digested 1.4 kb fragment derived from pTM002 was used as a probe for the another one. As a result, band patterns detected in two membranes were in good agreement showing that the objective region was cloned.

(4) Determination of Base Sequence

The base sequence of the cloned fragment of pTM004 was determined using a DNA sequencer (Pharmacia) after the reaction using an Auto Read DNA sequencing kit (Pharmacia). A primer was designed so as to be able to read from 3'-side to 5'-side based on the sequence that was obtained by using FITC-labeled RV primer attached in the kit. The sequence analysis was carried out serially. Another primer was designed so as to be able to read backward direction to perform a sequence analysis.

Figure 3:
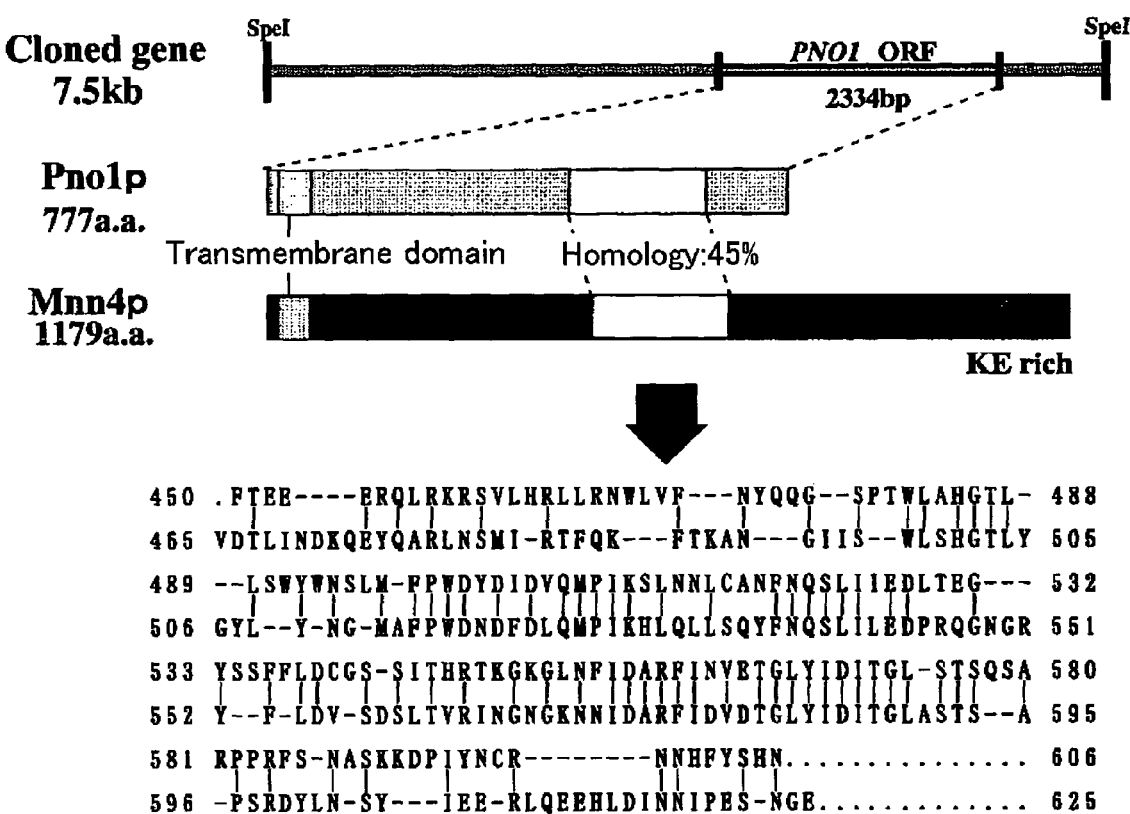
FIG. 3 illustrates homologous regions between PNO1 gene of a yeast belonging to the genus Pichia and MNN4 gene of S. cerevisiae.

DNASIS (Hitachi Soft Engineering) was used for the edition. Search for an open reading frame (ORF) based on the obtained base sequence (SEQ ID NO: 2 in the sequence listing) revealed that it codes a protein consisting of 777 amino acids. The amino acid sequence corresponding to the obtained base sequence is shown as SEQ ID NO: 3. This protein had a trans-membrane domain in its N terminal side. The region from the 450th amino acid to the 606th amino acid showed a homology value of 45% to *Saccharomyces cerevisiae* Mnn4 protein, while other region showed only a low homology value (FIG. 3).

This protein consisting of 777 amino acids was shorter than *Saccharomyces cerevisiae* Mnn4 protein consisting of 1137 amino acids. Moreover, KKKKEEEE repeated sequence in the C terminal side that plays an important role in the function of Mnn4 protein was not found in this protein [Jagami, Y. and Odani, T., Biochim. Biophys. Acta, 1426, 335–345 (1999)]. Although a part of the cloned gene is homologous to *Saccharomyces cerevisiae* MNN4 gene, the cloned gene is assumed to have (an) other function(s) and was named 'PNO1 gene'.

EXAMPLE 2

Preparation of PNO1 Gene-Controlled Yeast Strain Belonging to the Genus *Pichia*

(1) Preparation of Plasmid for Controlling PNO1 Gene

PNO1 gene-controlled strain was prepared to examine the properties of the strain and of an expressed protein so as to elucidate the function of PNO1 gene of a yeast strain belonging to the genus *Pichia*. For this purpose, PNO1 gene on the chromosome of a yeast belonging to the genus *Pichia* was disrupted as a controlling means. At the same time, it was planned to prepare a strain expressing human ATIII (antithrombin III) as an example of glycoprotein.

Figure 4:
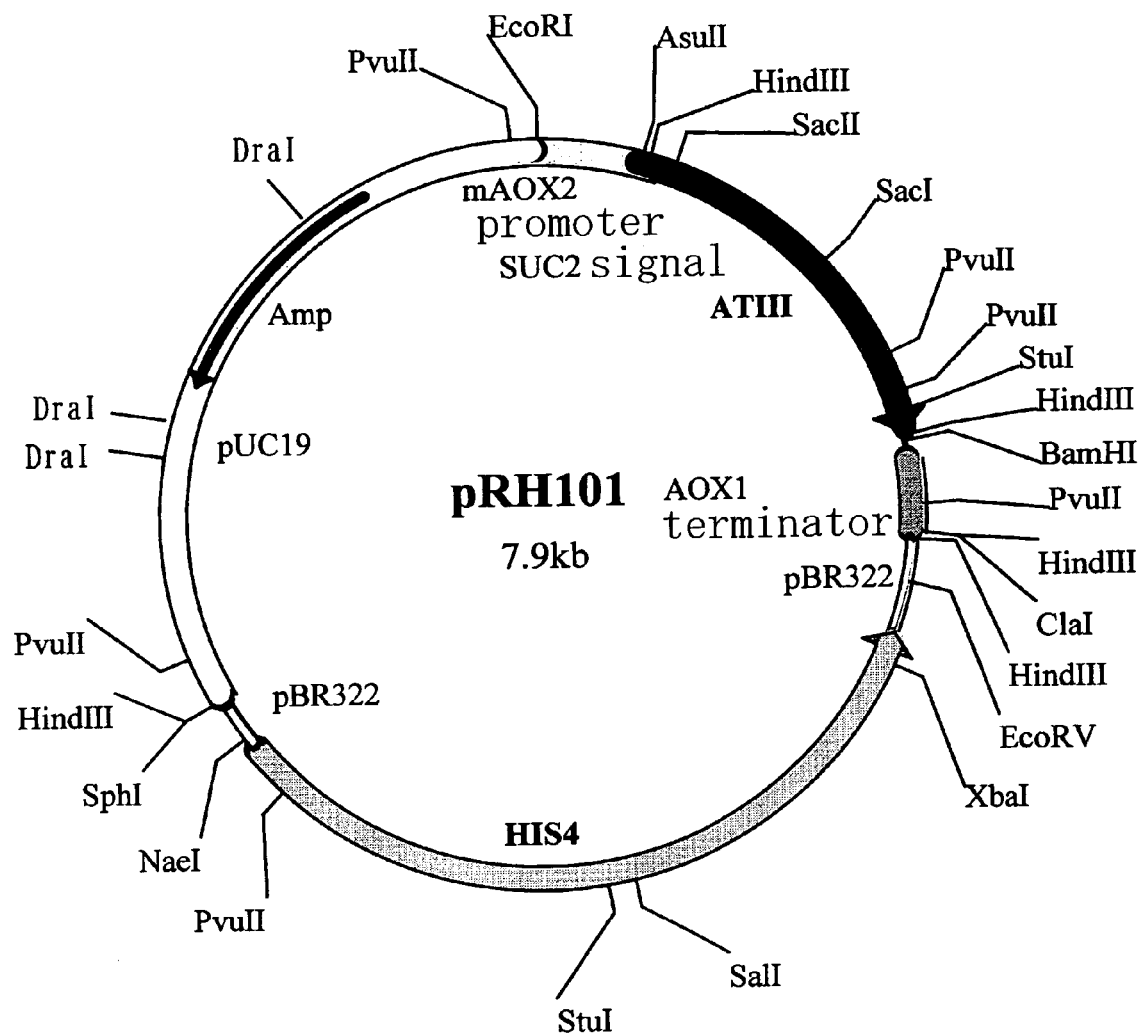
FIG. 4 illustrates plasmid pRH101 for expressing human antithrombin III (ATIII) gene in a yeast belonging to the genus Pichia.

ATIII is a single-stranded protein consisting of 432 amino acids with a molecular weight around 58 kDa that exists in normal human plasma at about 150 mg/L has four asparagine-linked sugar chain-addition sites. It has an activity of inhibiting a wide range of trypsin-type serine proteases including thrombin and Xa factor, and is a serum protease inhibitor playing an important role in the mechanism of controlling the blood coagulation. Vector pRH101 (FIG. 4) for expressing human ATIII gene in a yeast belonging to the genus *Pichia* was used as a material. Human ATIII gene is derived from pTY007 described in the literature [Yamauchi, T. et al., Biosci. Biotech. Biochem., 56, 600 (1992)]. The plasmid for controlling PNO1 gene was prepared as described below.

First, pTM004 digested with PstI and SmaI and pUC19 digested with PstI and SmaI were ligated using a DNA ligation kit (Takara Shuzo). *Escherichia coli* competent cell (DH5 Competent High, Toyobo) was transformed. Plasmids were extracted by the Mini-Prep method from colonies that appeared, and the target plasmid was selected and was named pTM006. pTM006 was digested with SacI and BamHI followed by blunting using a DNA blunting kit (Takara Shuzo) and carrying out a self-ligation to prepare pMM125.

Figure 5:
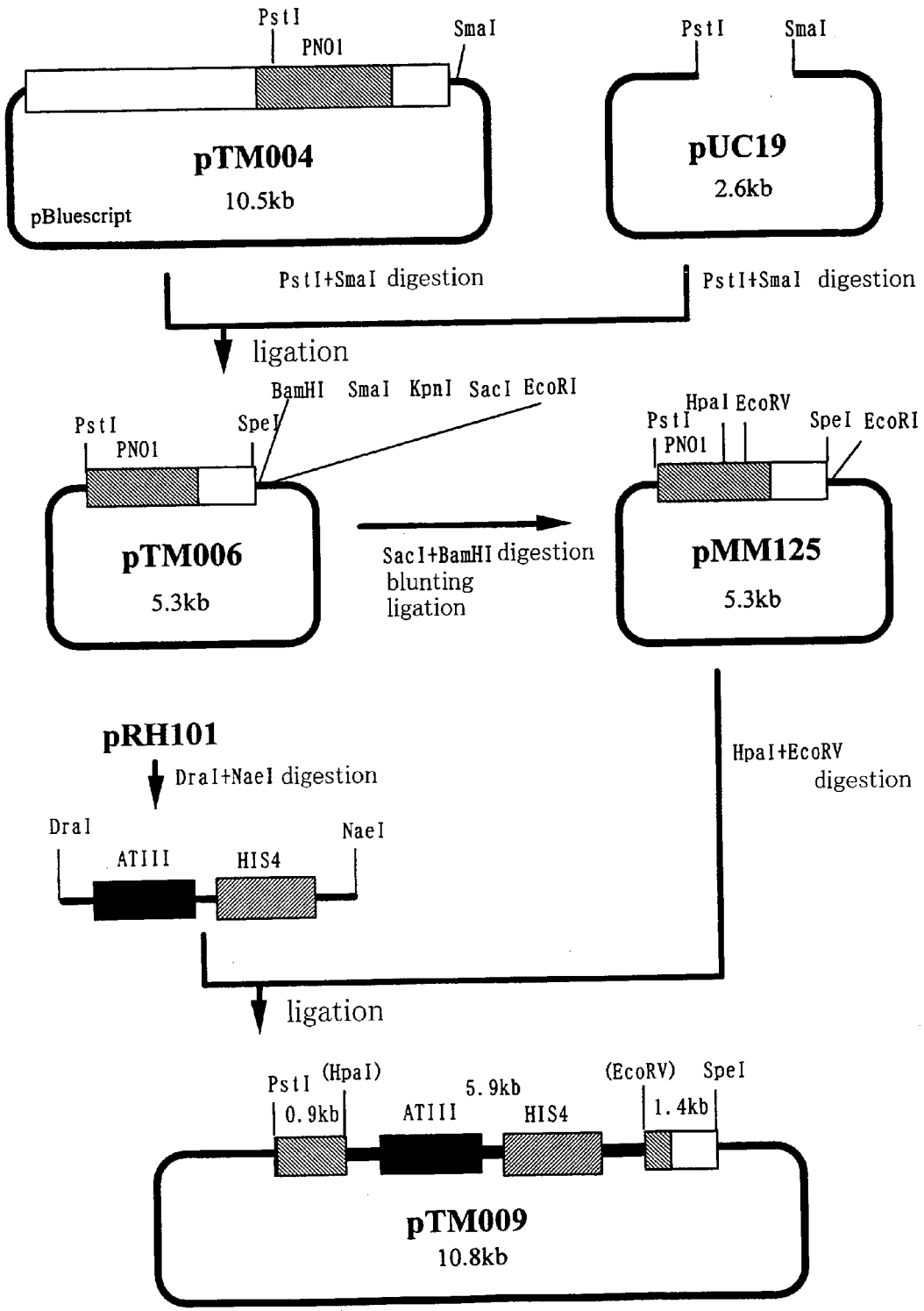
FIG. 5 illustrates the protocol for constructing plasmid pTM009, in which PNO1 gene is controlled, for human ATIII-expressing in a yeast belonging to the genus Pichia.

On the other hand, pRH101 was digested with DraI and NaeI to isolate a fragment containing HIS4 gene and ATIII expression unit that compose of mAOX2 promoter, SUC2 secretion leader sequence, human ATIII gene, and AOX1 terminator. In addition, pMM125 was digested with HpaI and EcoRV followed by ligation with the above fragment containing human ATIII expression unit and HIS4 gene, and then transformation of *Escherichia coli* was carried out using *E. coli* competent cell (DH5 Competent High, Toyobo). Plasmids were extracted by the Mini-Prep method from colonies that appeared, and the target plasmid was selected and was named pTM009 (FIG. 5).

(2) Preparation of PNO1 Gene-Controlled Yeast Strain Belonging to the Genus *Pichia*

Digestion of pTM009 was carried out with PstI and SpeI followed by transformation of yeast strain GTS115 belonging to the genus *Pichia* using a Yeast Maker Transformation Kit (Clontech) by the lithium chloride method. Cells were spread on a selection plate, and were incubated at 25° C. A clone that appeared was isolated to a single colony. The chromosomal DNA thereof was extracted using a Nucleon MiY Yeast DNA extraction kit (Amersham Pharmacia) and was digested with enzyme SpeI or with both enzymes SpeI and PstI to carry out electrophoresis and transfer to a nylon membrane. The Southern blotting analysis was carried out using a digoxigenin-labeled 0.6 kb fragment obtained by digesting pRH101 with SacII and SacI as an ATIII gene probe and a digoxigenin-labeled 1.5 kb fragment obtained by digesting pTM004 with EcoRI as a PNO1 gene probe.

Figure 6:
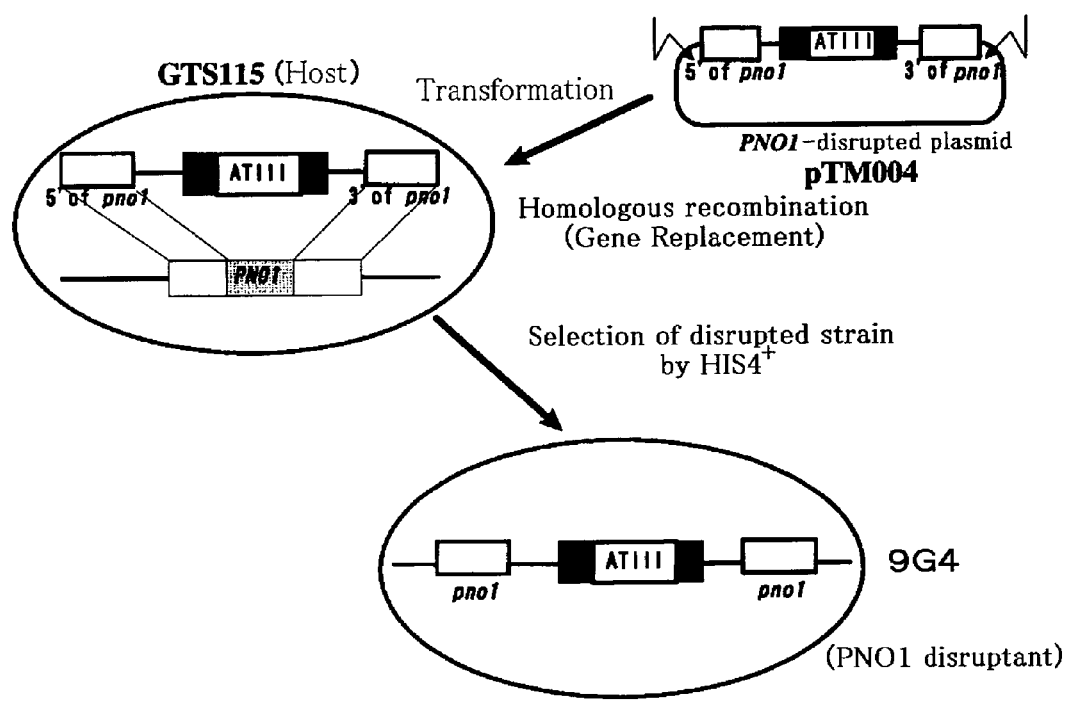
FIG. 6 illustrates the preparation of yeast strain 9G4 belonging to the genus Pichia, in which PNO1 gene is controlled, for expressing human ATIII.

A strain was selected, which gave a band of 13 kb in the membrane using SpeI in the case of an ATIII gene probe and gave a band of 8.2 kb in a membrane using both SpeI and PstI in the case of a PNO1 gene probe, and was named 'strain 9G4'. Strain 9G4 lacks 432 bp from HpaI site to EcoRV site of the chromosomal PNO1 gene, where ATIII expression unit and HIS4 gene are inserted instead them (FIG. 6).

EXAMPLE 3

Analyses of Properties of PNO1 Gene-Controlled Yeast Strain Belonging to the Genus *Pichia* and Produced Glycoprotein (1) Alcian Blue Staining of PNO1 Gene-Controlled Yeast Strain Belonging to the Genus *Pichia*

Alcian Blue is a basic phthalocyanine-based dye. Alcian Blue staining is used as a simple method for evaluating a degree of phosphate group that gives a major negative charge in the cell wall [Ballou, C. E., Methods in Enzymology, 185, 440–470 (1990)]. Although Alcian Blue stains cells of a wild-type *Saccharomyces cerevisiae*, but it does not stain cells of *S. cerevisiae* MNN4 gene mutant. These results show that the phosphorylation of sugar outer chain was suppressed in the latter case. Therefore, the staining properties of PNO1 gene-controlled yeast strain belonging to the genus *Pichia* were compared with that of a wild-type yeast strain belonging to the genus *Pichia* or *S. cerevisiae* MNN4 gene mutant.

Each of PNO1 gene-controlled strain 9G4, wild-type yeast belonging to the genus *Pichia* strain GTS115, and *Saccharomyces cerevisiae* MNN4 gene mutant strain LB6-5D (MATα, mnn4-1, suc2, ma1, CUP1) (ATCC 52524) was cultured in 3 mL of YPD medium for 72 h. Cells were harvested and were stained with 0.1% Alcian Blue solution in 0.02N hydrochloric acid at room temperature for 20 mm, resulting that strain LB6-5D remained white, while strains GTS 115 and 9G4 were stained blue to similar extents. This result indicated that the PNO1 gene-controlled strain and strain LB6-5D have different cell surface sugar chains, i.e., Pno1 protein is different from Mnn4 protein, and dose not so participate in phosphorylation of sugar outer chain.

(2) Preparation of Recombinant Human ATIII-Producing Wild-Type Yeast Strain Belonging to the Genus *Pichia*

A recombinant human ATIII-producing wild-type yeast strain belonging to the genus *Pichia* was prepared in order to have a control for the comparison with the recombinant human ATIII produced by the PNO1 gene-controlled yeast strain belonging to the genus *Pichia*. A human ATIII expression plasmid pRH101 (FIG. 4) was digested with SalI, and was transformed into *P. pastoris* strain GTS115 using the lithium chloride method. A strain that one copy of pRH101 was integrated into chromosomal his4 gene locus was selected by the Southern blotting analysis, and was named 'strain RH101'.

(3) Jar Fermenter Culture and Purification of Recombinant Human ATIII

Figure 7:
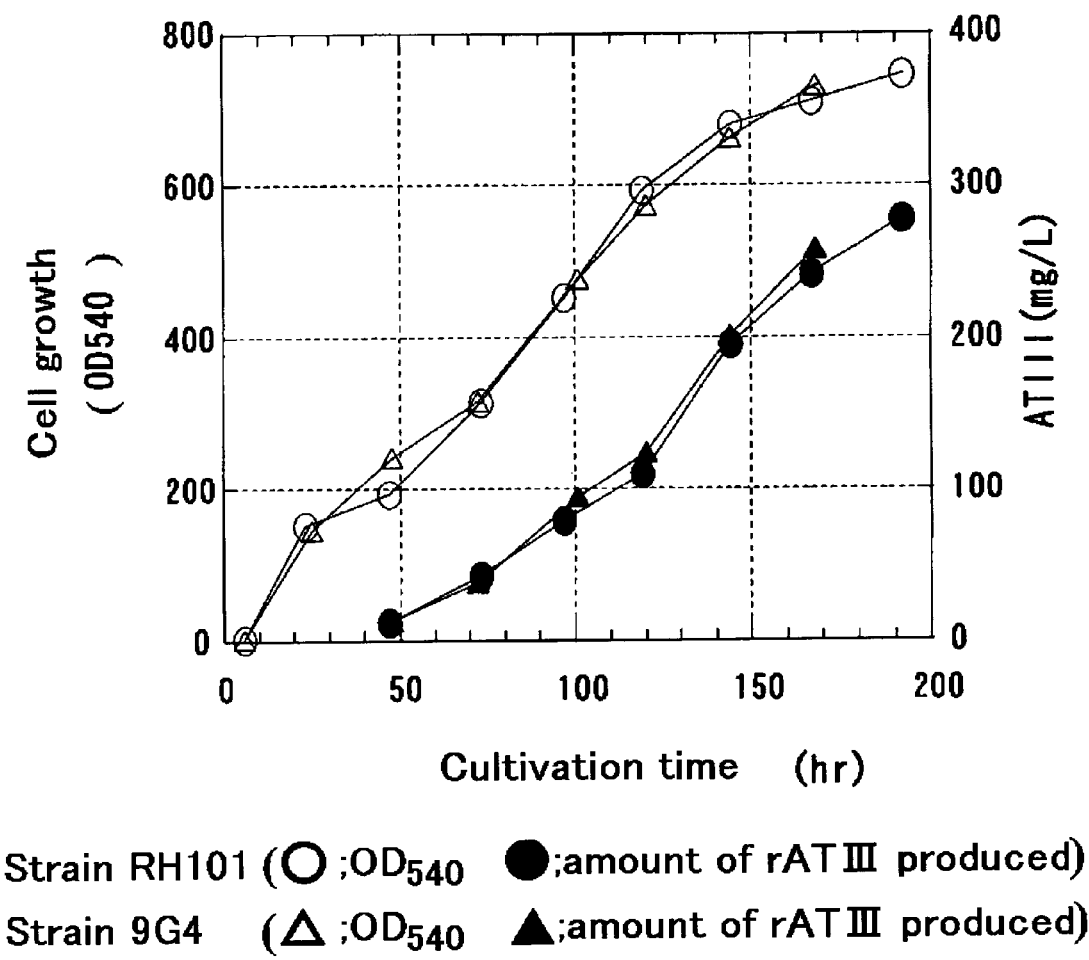
FIG. 7 illustrates culture profiles of strains RH101 and 9G4 using jar fermenters.

Each of human ATIII-producing wild-type yeast strain RH101 belonging to the genus *Pichia* and human ATIII-producing PNO1 gene-controlled strain 9G4 was cultured using a 3-L jar fermenter (BMD-3, ABLE corp.). Cells were proliferated in a medium containing glycerol, followed by feeding a medium containing methanol as a carbon source. The degree of proliferation as measured by $OD_{540}$ and the amount of ATIII produced as measured by the ELISA method (enzyme-linked immunosorbent assay method), are illustrated in FIG. 7. Strains RH101 and 9G4 showed similar profiles with respect to the degree of proliferation and the amount of ATIII produced, and no remarkable difference by controlling PNO1 gene was observed.

Each of strains 9G4 and RH101 was proliferated in the jar fermenter until an $OD_{540}$ value reaches 700, and the culture supernatant was collected. Analyzing the culture supernatant by SDS-PAGE and Western blotting permitted detecting a major fraction of produced recombinant ATIII at the same position as that of ATIII derived from plasma as well as a minor fraction of highly glycosylated polymer with respect to both strains. The major fraction was purified by the heparin column chromatography, the cation-exchange chromatography, the gel filtration, and the ultrafiltration sequentially in this order to give a purified product of recombinant ATIII.

Figure 8:
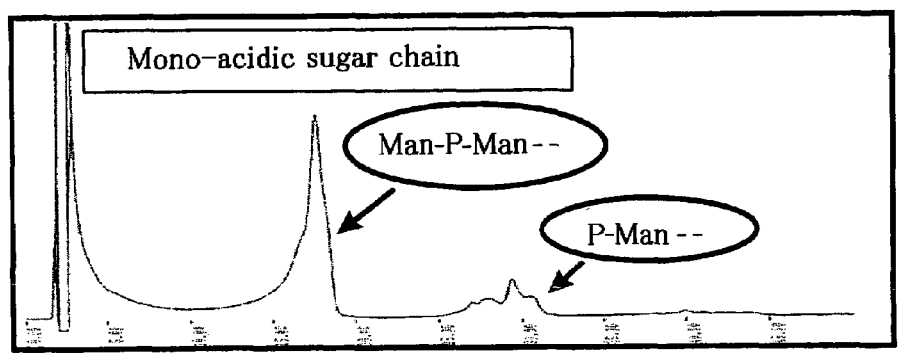
FIG. 8 illustrates results of the analysis of (A) products after enzymatic reaction, (B) products after acid treatment, and (C) products after treatment with acid and alkaline phosphatase, of recombinant ATIII derived from a wild-type yeast belonging to the genus Pichia.

(4) Confirmation of Phosphate Addition to Sugar Chain of Recombinant Human ATIII Produced by Wild-Type Yeast Using the purified product of recombinant ATIII produced by strain RH101, the sugar chain was cleaved using Glycopeptidase F (Takara Shuzo) [Plummer, T. H. Jr., et al., J. Biol. Chem., 259, 10700–10704 (1984)]. The sugar chain was purified using a cellulose cartridge glycan preparation kit (Takara Shuzo), and the reducing end was labeled with 2-aminopyridine ('pyridylaminated') [Hase, S., et al., J. Biochem., 85, 217–220 (1979)]. The analysis using an anion-exchange column (DEAE-5PW, Toso) [Nakagawa, H., et al., Anal. Biochem., 226, 130–138 (1995)] revealed that the sugar chain contains not only a neutral sugar chain but also two kinds or more of acidic sugar chain (FIG. 8A).

The fraction that is considered to have an electric charge of 1 was purified, and was acid-hydrolyzed with 0.1N hydrochloric acid at 100° C. for 30 min. It is known that this reaction cleaves the bond between mannose (Man) and phosphate at a non-reducing end [Tieme, T. R. et al., Biochemistry, 10, 4121–4129 (1971)]. After the reaction, the sugar chain was converted to an acidic sugar chain having a phosphate group at the non-reducing end. At this time, the electric charge became 2 (FIG. 8B). Then, 0.6 unit of an alkaline phosphatase (Takara Shuzo) that is an enzyme hydrolyzing the terminal phosphate group was affected in a 50 mM Tris-HCl, pH9, 1 mM $MgCl_2$ solution at 65° C. for 3 h. This reaction removed the phosphate group to give a neutral sugar chain. Thus, it was revealed that the acidic sugar chain having been added to recombinant ATIII is phosphorylated (FIG. 8C).

(5) Comparison of Phosphorylation in Sugar Chain Between Recombinant Human ATIII Derived from Wild-Type Yeast and Recombinant Human ATIII Derived from PNO1 Gene-Controlled Strain A purified product of recombinant ATIII produced by strain RH101 or 9G4 was pyridylaminated in a manner similar to one described above. A neutral sugar chain and an acidic sugar chain were separated each other by the anion column chromatography (DEAE-5PW, Toso). Finally, the specimens were analyzed using an amide column (Amide-80, Toso) that permits eluting sugar chains in the order of size [Tomiya, N. et al., Anal. Biochem., 171, 73–90 (1988)] to compare areas of sugar chains of both strains.

Figure 9:
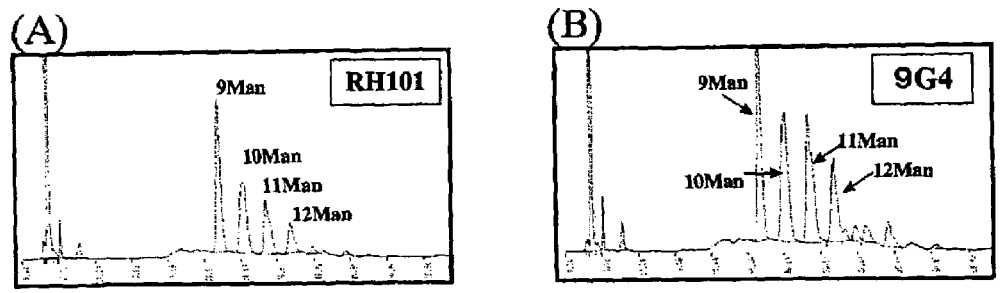
FIG. 9 illustrates structural analyses of sugar chains of recombinant ATIII derived from a wild type yeast belonging to the genus Pichia and recombinant ATIII derived from a PNO1 gene-controlled strain. Application amounts of (A) and (B) were ⅕ of those of (C) and (D).
Figure 9:
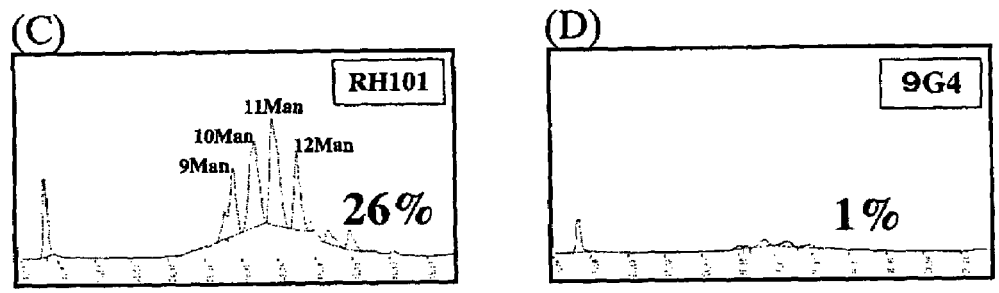

Neutral sugar chain fractions were estimated to be high-mannose sugar chains mainly consisting of 9 to 12 molecules of mannose (FIGS. 9A and B). Contents of acidic sugar chain having been added to recombinant ATIII derived from strains RH101 and 9G4 were calculated using the equation (total area of acidic sugar chain)/(total area of neutral sugar chain+total area of acidic sugar chain), with strain RH101 being 26% and strain 9G4 being 1%, i.e., the content of acidic sugar chain was quite reduced in the latter (FIG. 9).

The above result shows that the number of phosphate groups added to the core-like sugar chain of the glycoprotein produced by the PNO1 gene-controlled strain is remarkably reduced compared with that of wild-type yeast. The percentage of acidic sugar chain added to the core-like sugar chain per total sugar chain was less than 30 with respect to *Saccharomyces cerevisiae* MNN4 gene-controlled strain [Japan Patent Laid Open Hei 9-266792], while that of PNO1 gene-controlled yeast strain belonging to the genus *Pichia* was 1, i.e., the method according to the present invention was more excellent than the conventional method for reducing the acidic sugar chain.

The degree of the reduction of the acidic sugar chain added to the core-like sugar chain with respect to the *Saccharomyces cerevisiae* MNN4 gene-controlled strain was less than the wild type strain [Japan Patent Laid Open Hei 9-266792], while that of the PNO1 gene-controlled yeast strain belonging to the genus *Pichia* was 1/26 of that of the wild-type strain, i.e., the acidic sugar chain was considerably reduced. The homology between *S. cerevisiae* MNN4 gene and PNO1 gene of a yeast belonging to the genus *Pichia* is low excepting some parts, and the degrees of the Alcian Blue staining are different between the *Saccharomyces cerevisiae* MNN4 gene-controlled strain and the PNO1 gene-controlled yeast strain belonging to the genus *Pichia*. Therefore, it was suggested that PNO1 gene is a novel gene having a function different from that of MNN4 gene.

(6) Comparison of Antigenicity Between Recombinant Human ATIII Derived from Wild-Type Yeast and Recombinant Human ATIII Derived from PNO1 Gene-Controlled Strain Antisera against each recombinant human ATIII were obtained by immunizing recombinant human ATIII derived from a wild-type yeast belonging to the genus *Pichia* and recombinant human ATIII derived from a PNO1 gene-controlled strain to 12-weeks-old Japanese white male rabbits (Kitayama Rabes) together with aluminum hydroxide gel adjuvant (SERAVA).

The inhibition of the reaction of each antiserum with an antigen by human ATIII derived from plasma, i.e., the inhibition of the binding reaction of an immobilized recombinant human ATIII derived from a wild-type yeast belonging to the genus *Pichia* or recombinant human ATIII derived from a PNO1 gene-controlled strain with an antiserum by human ATIII derived from plasma, was evaluated by ELISA. As a result, it was revealed that inhibition occurs at a lower concentration of human ATIII derived from plasma in the reaction with anti-recombinant human ATIII antibody derived from PNO1 gene-controlled strain than in the reaction with anti-recombinant human ATIII antibody derived from a wild-type yeast belonging to the genus *Pichia* (FIG. 10). Therefore, it was considered that an epitope specific to recombinant human ATIII derived from a yeast is diminished in recombinant human ATIII derived from a yeast compared with recombinant human ATIII derived from a wild-type yeast belonging to the genus *Pichia*.

INDUSTRIAL APPLICABILITY

The present invention provides a protein participating in the addition of mannose phosphate to the sugar chain of a glycoprotein derived from a yeast belonging to the genus *Pichia* and a gene coding the protein for the first time. Providing the protein participating in the addition of mannose phosphate to the sugar chain of the glycoprotein and the gene coding the protein is useful because it can be a basis for elucidating the mechanism of the addition of mannose phosphate to the sugar chain of the glycoprotein in yeast. The present invention permits providing a yeast belonging to the genus *Pichia* producing a pharmaceutically useful glycoprotein by remarkably reducing the addition of phosphate to the sugar chain. Using a yeast strain belonging to the genus *Pichia* according to the present invention permits production of pharmaceutically useful glycoprotein with remarkable reduction of the phosphate addition to sugar chain. A glycoprotein produced by using a means according to the present invention has sugar chain in which the addition of phosphate is remarkably reduced, so that the glycoprotein is considered to be less antigenic to human beings and mammalians, and is pharmaceutically useful.

What is claimed is:

1. A method for controlling the formation of an acidic sugar chain in a yeast belonging to the genus *Pichia*, wherein a gene participating at least in the addition of mannose phosphate to a sugar chain in a core-like sugar chain of a glycoprotein is controlled, said gene encoding an amino acid sequence comprising SEQ ID NO: 1 wherein said gene is controlled by mutating the polynucleotide comprising from the 150th to the 2480th nucleotide of SEQ ID NO: 2, by introducing at least one mutation, including deletion substitution, insertion, or addition, into the gene to reduce the amount of acidic sugar in said glycoprotein.

2. The method according to claim 1, wherein controlling the gene comprises introducing at least one mutation, including deletion, substitution, insertion, or addition, into the gene to reduce the ratio of acidic sugar chain to total sugar chain at least in the core-like sugar chain of a said glycoprotein to 10% or less.

* * * * *

UNITED STATES PATENT AND TRADEMARK OFFICE
CERTIFICATE OF CORRECTION

PATENT NO. : 7,198,921 B2  Page 1 of 1
APPLICATION NO. : 10/276075
DATED : April 3, 2007
INVENTOR(S) : Miura et al.

It is certified that error appears in the above-identified patent and that said Letters Patent is hereby corrected as shown below:

TITLE PAGE
ADD THE FOREIGN APPLICATION PRIORITY DATA SECTION:

(30) --JP2000-144643 May 17, 2000--.

Signed and Sealed this

Twenty-first Day of August, 2007

JON W. DUDAS
*Director of the United States Patent and Trademark Office*